United States Patent
Johnson

(10) Patent No.: US 9,248,162 B2
(45) Date of Patent: Feb. 2, 2016

(54) FACTOR H FOR TREATMENT OF RHEUMATOID ARTHRITIS

(71) Applicants: Baxter International Inc., Deerfield, IL (US); Baxter Healthcare SA, Glattpark (Opfikon) (CH)

(72) Inventor: Richard Johnson, Mundelein, IL (US)

(73) Assignees: Baxalta Incorporated, Bannockburn, IL (US); Baxalta GmbH, Glattpark (Opfikon) (CH)

( * ) Notice: Subject to any disclaimer, the term of this patent is extended or adjusted under 35 U.S.C. 154(b) by 0 days.

(21) Appl. No.: 14/210,091

(22) Filed: Mar. 13, 2014

(65) Prior Publication Data

US 2014/0336121 A1 Nov. 13, 2014

Related U.S. Application Data

(60) Provisional application No. 61/786,023, filed on Mar. 14, 2013.

(51) Int. Cl.
| | |
|---|---|
| *A61K 38/17* | (2006.01) |
| *C07K 14/00* | (2006.01) |
| *A61P 19/02* | (2006.01) |
| *A61K 38/13* | (2006.01) |

(52) U.S. Cl.
CPC ............ *A61K 38/1725* (2013.01); *A61K 38/13* (2013.01); *A61K 38/1709* (2013.01)

(58) Field of Classification Search
CPC . A61K 38/1725; A61K 38/1709; A61K 38/13
See application file for complete search history.

(56) References Cited

U.S. PATENT DOCUMENTS

| | | | |
|---|---|---|---|
| 7,351,524 B2 | 4/2008 | Hageman et al. | |
| 7,745,389 B2 | 6/2010 | Hageman | |
| 2011/0021432 A1* | 1/2011 | Bairstow et al. | 514/15.3 |
| 2011/0229497 A1* | 9/2011 | Thurman et al. | 424/178.1 |

FOREIGN PATENT DOCUMENTS

| | | |
|---|---|---|
| EP | 0 222 611 A2 | 5/1987 |
| WO | WO 00/52479 A2 | 3/2000 |
| WO | WO 03/068150 A2 | 8/2003 |
| WO | WO 03/068150 A3 | 8/2003 |
| WO | WO 2006/062716 A2 | 6/2006 |
| WO | WO 2007/066017 A2 | 6/2007 |
| WO | WO 2007/149567 A2 | 12/2007 |
| WO | WO 2008/113589 A1 | 9/2008 |
| WO | WO 2011/011753 A1 | 1/2011 |

OTHER PUBLICATIONS

Annette Büttner-Mainik et al, Production of biologically active recombinant human factor H in Physcomitrella, Plant Biotechnology Journal, 2011, 9, pp. 373-383.*
Stephens et al, Musculoskeletal Injections: A Review of the Evidence, Am Fam Physician, 2008, 78, pp. 971-976.*
Banda, N.K. et al., "Essential Role of Surface-Bound Complement Factor H in Controlling Immune Complex-Induced Arthritis," *The Journal of Immunology*, 2013, vol. 190, pp. 3560-3569.
Banda, N.K. et al., "Targeted Inhibition of the Complement Alternative Pathway with Complement Receptor 2 and Factor H Attenuates Collagen Antibody-Induced Arthritis in Mice," *The Journal of Immunology*, 2009, vol. 183, pp. 5928-5937.
Friese, M.A. et al., "Release of endogenous anti-inflammatory complement regulators FHL-1 and factor H protects synovial fibroblasts during rheumatoid arthritis," *Clin Exp Immunol*, 2003, vol. 132, pp. 485-495.
International Search Report mailed Aug. 29, 2014, for International Patent Application No. PCT/US2014/026681, 5 pages.
Ripoche, J. et al., "The complete amino acid sequence of human complement factor H," *Biochem. J.*, 1988, vol. 249, pp. 593-602.

* cited by examiner

*Primary Examiner* — Julie Ha
*Assistant Examiner* — Li Ni Komatsu
(74) *Attorney, Agent, or Firm* — Morgan, Lewis & Bockius LLP

(57) ABSTRACT

The present invention provides a method for preventing or inhibiting allograft rejection by a recipient of that allograft by treating the recipient with a composition comprising Factor H (FH). The invention also encompasses methods in which the recipient is also administered one or more immunosuppressants in addition to the Factor H.

21 Claims, 12 Drawing Sheets

MRLLAKIICLMLWAICVAEDCNELPPRRNTEILTGSWSDQTYPEGTQAIYKCRPGYRSLG
NIIMVCRKGEWVALNPLRKQKRPCGHPGDTPFGTFTLTGGNVFEYGVKAVYTCNEGYQ
LLGEINYRECDTDGWTNDIPICEVVKCLPVTAPENGKIVSSAMEPDREYHFGQAVRFVC
NSGYKIEGDEEMHCSDDGFWSKEKPKCVEISCKSPDVINGSPISQKIIYKENERFQYKCN
MGYEYSERGDAVCTESGWRPLPSCEEKSCDNPYIPNGDYSPLRIKHRTGDEITYQCRNG
FYPATRGNTAKCTSTGWIPAPRCTLKPCDYPDIKHGGLYHENMRRPYFPVAVGKYYSY
YCDEHFETPSGSYWDHIHCTQDGWSPAVPCLRKCYFPYLENGYNQNYGRKFVQGKSID
VACHPGYALPKAQTTVTCMENGWSPTPRCIRVKTCSKSSIDIENGFISESQYTYALKEKA
KYQCKLGYVTADGETSGSIRCGKDGWSAQPTCIKSCDIPVFMNARTKNDFTWFKLNDT
LDYECHDGYESNTGSTTGSIVCGYNGWSDLPICYERECELPKIDVHLVPDRKKDQYKVG
EVLKFSCKPGFTIVGPNSVQCYHFGLSPDLPICKEQVQSCGPPPELLNGNVKEKTKEEYG
HSEVVEYYCNPRFLMKGPNKIQCVDGEWTTLPVCIVEESTCGDIPELEHGWAQLSSPPY
YYGDSVEFNCSESFTMIGHRSITCIHGVWTQLPQCVAIDKLKKCKSSNLIILEEHLKNKKE
FDHNSNIRYRCRGKEGWIHTVCINGRWDPEVNCSMAQIQLCPPPPQIPNSHNMTTTLNY
RDGEKVSVLCQENYLIQEGEEITCKDGRWQSIPLCVEKIPCSQPPQIEHGTINSSRSSQESY
AHGTKLSYTCEGGFRISEENETTCYMGKWSSPPQCEGLPCKSPPEISHGVVAHMSDSYQ
YGEEVTYKCFEGFGIDGPAIAKCLGEKWSHPPSCIKTDCLSLPSFENAIPMGEKKDVYKA
GEQVTYTCATYYKMDGASNVTCINSRWTGRPTCRDTSCVNPPTVQNAYIVSRQMSKYP
SGERVRYQCRSPYEMFGDEEVMCLNGNWTEPPQCKDSTGKCGPPPPIDNGDITSFPLSV
YAPASSVEYQCQNLYQLEGNKRITCRNGQWSEPPKCLHPCVISREIMENYNIALRWTAK
QKLYSRTGESVEFVCKRGYRLSSRSHTLRTTCWDGKLEYPTCAKR (SEQ ID NO: 1).

FIGURE 12

SEQUENCE LISTING

```
<160> NUMBER OF SEQ ID NOS: 1

<210> SEQ ID NO 1
<211> LENGTH: 1230
<212> TYPE: PRT
<213> ORGANISM: Artificial Sequence
<220> FEATURE:
<223> OTHER INFORMATION: Synthetic Factor H variant

<400> SEQUENCE: 1

Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
            20                  25                  30

Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Ile Ile Met
    50                  55                  60

Val Cys Arg Lys Gly Glu Trp Val Ala Leu Asn Pro Leu Arg Lys Gln
65                  70                  75                  80

Lys Arg Pro Cys Gly His Pro Gly Asp Thr Pro Phe Gly Thr Phe Thr
                85                  90                  95

Leu Thr Gly Gly Asn Val Phe Glu Tyr Gly Val Lys Ala Val Tyr Thr
            100                 105                 110

Cys Asn Glu Gly Tyr Gln Leu Leu Gly Glu Ile Asn Tyr Arg Glu Cys
        115                 120                 125

Asp Thr Asp Gly Trp Thr Asn Asp Ile Pro Ile Cys Glu Val Val Lys
    130                 135                 140

Cys Leu Pro Val Thr Ala Pro Glu Asn Gly Lys Ile Val Ser Ser Ala
145                 150                 155                 160

Met Glu Pro Asp Arg Glu Tyr His Phe Gly Gln Ala Val Arg Phe Val
                165                 170                 175
```

-continued

```
Cys Asn Ser Gly Tyr Lys Ile Glu Gly Asp Glu Met His Cys Ser
            180                 185                 190
Asp Asp Gly Phe Trp Ser Lys Glu Lys Pro Lys Cys Val Glu Ile Ser
        195                 200                 205
Cys Lys Ser Pro Asp Val Ile Asn Gly Ser Pro Ile Ser Gln Lys Ile
    210                 215                 220
Ile Tyr Lys Glu Asn Glu Arg Phe Gln Tyr Lys Cys Asn Met Gly Tyr
225                 230                 235                 240
Glu Tyr Ser Glu Arg Gly Asp Ala Val Cys Thr Glu Ser Gly Trp Arg
            245                 250                 255
Pro Leu Pro Ser Cys Glu Glu Lys Ser Cys Asp Asn Pro Tyr Ile Pro
        260                 265                 270
Asn Gly Asp Tyr Ser Pro Leu Arg Ile Lys His Arg Thr Gly Asp Glu
    275                 280                 285
Ile Thr Tyr Gln Cys Arg Asn Gly Phe Tyr Pro Ala Thr Arg Gly Asn
290                 295                 300
Thr Ala Lys Cys Thr Ser Thr Gly Trp Ile Pro Ala Pro Arg Cys Thr
305                 310                 315                 320
Leu Lys Pro Cys Asp Tyr Pro Asp Ile Lys His Gly Gly Leu Tyr His
            325                 330                 335
Glu Asn Met Arg Arg Pro Tyr Phe Pro Val Ala Val Gly Lys Tyr Tyr
        340                 345                 350
Ser Tyr Tyr Cys Asp Glu His Phe Glu Thr Pro Ser Gly Ser Tyr Trp
    355                 360                 365
Asp His Ile His Cys Thr Gln Asp Gly Trp Ser Pro Ala Val Pro Cys
370                 375                 380
Leu Arg Lys Cys Tyr Phe Pro Tyr Leu Glu Asn Gly Tyr Asn Gln Asn
385                 390                 395                 400
Tyr Gly Arg Lys Phe Val Gln Gly Lys Ser Ile Asp Val Ala Cys His
            405                 410                 415
Pro Gly Tyr Ala Leu Pro Lys Ala Gln Thr Thr Val Thr Cys Met Glu
        420                 425                 430
Asn Gly Trp Ser Pro Thr Pro Arg Cys Ile Arg Val Lys Thr Cys Ser
    435                 440                 445
Lys Ser Ser Ile Asp Ile Glu Asn Gly Phe Ile Ser Glu Ser Gln Tyr
450                 455                 460
Thr Tyr Ala Leu Lys Glu Lys Ala Lys Tyr Gln Cys Lys Leu Gly Tyr
465                 470                 475                 480
Val Thr Ala Asp Gly Glu Thr Ser Gly Ser Ile Arg Cys Gly Lys Asp
            485                 490                 495
Gly Trp Ser Ala Gln Pro Thr Cys Ile Lys Ser Cys Asp Ile Pro Val
        500                 505                 510
Phe Met Asn Ala Arg Thr Lys Asn Asp Phe Thr Trp Phe Lys Leu Asn
    515                 520                 525
Asp Thr Leu Asp Tyr Glu Cys His Asp Gly Tyr Glu Ser Asn Thr Gly
530                 535                 540
Ser Thr Thr Gly Ser Ile Val Cys Gly Tyr Asn Gly Trp Ser Asp Leu
545                 550                 555                 560
Pro Ile Cys Tyr Glu Arg Glu Cys Glu Leu Pro Lys Ile Asp Val His
            565                 570                 575
Leu Val Pro Asp Arg Lys Lys Asp Gln Tyr Lys Val Gly Glu Val Leu
        580                 585                 590
```

```
Lys Phe Ser Cys Lys Pro Gly Phe Thr Ile Val Gly Pro Asn Ser Val
            595                 600                 605

Gln Cys Tyr His Phe Gly Leu Ser Pro Asp Leu Pro Ile Cys Lys Glu
    610                 615                 620

Gln Val Gln Ser Cys Gly Pro Pro Glu Leu Leu Asn Gly Asn Val
625                 630                 635                 640

Lys Glu Lys Thr Lys Glu Glu Tyr Gly His Ser Glu Val Val Glu Tyr
                645                 650                 655

Tyr Cys Asn Pro Arg Phe Leu Met Lys Gly Pro Asn Lys Ile Gln Cys
            660                 665                 670

Val Asp Gly Glu Trp Thr Thr Leu Pro Val Cys Ile Val Glu Glu Ser
        675                 680                 685

Thr Cys Gly Asp Ile Pro Glu Leu Glu His Gly Trp Ala Gln Leu Ser
    690                 695                 700

Ser Pro Pro Tyr Tyr Tyr Gly Asp Ser Val Glu Phe Asn Cys Ser Glu
705                 710                 715                 720

Ser Phe Thr Met Ile Gly His Arg Ser Ile Thr Cys Ile His Gly Val
                725                 730                 735

Trp Thr Gln Leu Pro Gln Cys Val Ala Ile Asp Lys Leu Lys Lys Cys
            740                 745                 750

Lys Ser Ser Asn Leu Ile Ile Leu Glu Glu His Leu Lys Asn Lys Lys
        755                 760                 765

Glu Phe Asp His Asn Ser Asn Ile Arg Tyr Arg Cys Arg Gly Lys Glu
    770                 775                 780

Gly Trp Ile His Thr Val Cys Ile Asn Gly Arg Trp Asp Pro Glu Val
785                 790                 795                 800

Asn Cys Ser Met Ala Gln Ile Gln Leu Cys Pro Pro Pro Gln Ile
                805                 810                 815

Pro Asn Ser His Asn Met Thr Thr Thr Leu Asn Tyr Arg Asp Gly Glu
            820                 825                 830

Lys Val Ser Val Leu Cys Gln Glu Asn Tyr Leu Ile Gln Glu Gly Glu
        835                 840                 845

Glu Ile Thr Cys Lys Asp Gly Arg Trp Gln Ser Ile Pro Leu Cys Val
    850                 855                 860

Glu Lys Ile Pro Cys Ser Gln Pro Pro Gln Ile Glu His Gly Thr Ile
865                 870                 875                 880

Asn Ser Ser Arg Ser Ser Gln Glu Ser Tyr Ala His Gly Thr Lys Leu
                885                 890                 895

Ser Tyr Thr Cys Glu Gly Gly Phe Arg Ile Ser Glu Glu Asn Glu Thr
            900                 905                 910

Thr Cys Tyr Met Gly Lys Trp Ser Pro Pro Gln Cys Glu Gly Leu
        915                 920                 925

Pro Cys Lys Ser Pro Pro Glu Ile Ser His Gly Val Val Ala His Met
    930                 935                 940

Ser Asp Ser Tyr Gln Tyr Gly Glu Glu Val Thr Tyr Lys Cys Phe Glu
945                 950                 955                 960

Gly Phe Gly Ile Asp Gly Pro Ala Ile Ala Lys Cys Leu Gly Glu Lys
                965                 970                 975

Trp Ser His Pro Pro Ser Cys Ile Lys Thr Asp Cys Leu Ser Leu Pro
            980                 985                 990

Ser Phe Glu Asn Ala Ile Pro Met Gly Glu Lys Lys Asp Val Tyr Lys
        995                 1000                1005
```

```
Ala Gly Glu Gln Val Thr Tyr Thr Cys Ala Thr Tyr Tyr Lys Met
    1010            1015            1020
Asp Gly Ala Ser Asn Val Thr Cys Ile Asn Ser Arg Trp Thr Gly
    1025            1030            1035
Arg Pro Thr Cys Arg Asp Thr Ser Cys Val Asn Pro Pro Thr Val
    1040            1045            1050
Gln Asn Ala Tyr Ile Val Ser Arg Gln Met Ser Lys Tyr Pro Ser
    1055            1060            1065
Gly Glu Arg Val Arg Tyr Gln Cys Arg Ser Pro Tyr Glu Met Phe
    1070            1075            1080
Gly Asp Glu Glu Val Met Cys Leu Asn Gly Asn Trp Thr Glu Pro
    1085            1090            1095
Pro Gln Cys Lys Asp Ser Thr Gly Lys Cys Gly Pro Pro Pro Pro
    1100            1105            1110
Ile Asp Asn Gly Asp Ile Thr Ser Phe Pro Leu Ser Val Tyr Ala
    1115            1120            1125
Pro Ala Ser Ser Val Glu Tyr Gln Cys Gln Asn Leu Tyr Gln Leu
    1130            1135            1140
Glu Gly Asn Lys Arg Ile Thr Cys Arg Asn Gly Gln Trp Ser Glu
    1145            1150            1155
Pro Pro Lys Cys Leu His Pro Cys Val Ile Ser Arg Glu Ile Met
    1160            1165            1170
Glu Asn Tyr Asn Ile Ala Leu Arg Trp Thr Ala Lys Gln Lys Leu
    1175            1180            1185
Tyr Ser Arg Thr Gly Glu Ser Val Glu Phe Val Cys Lys Arg Gly
    1190            1195            1200
Tyr Arg Leu Ser Ser Arg Ser His Thr Leu Arg Thr Thr Cys Trp
    1205            1210            1215
Asp Gly Lys Leu Glu Tyr Pro Thr Cys Ala Lys Arg
    1220            1225            1230
```

FACTOR H FOR TREATMENT OF RHEUMATOID ARTHRITIS

CROSS REFERENCE TO RELATED APPLICATION

This application claims priority to U.S. Patent Application No. 61/786,023, filed Mar. 14, 2013, the contents of which are incorporated by reference in their entirety for all purposes.

BACKGROUND OF THE INVENTION

The complement system is uniquely designed to recognize, destroy and facilitate the removal of pathogens that are constantly trying to invade our bodies. The system is composed of approximately 30 plasma and cell surface proteins that incorporate both humoral and cellular effector mechanisms to provide redundant and highly efficient protection from infection. Analogous to the clotting cascade, the complement system is activated by association of specific proteins to form active complexes, generally with serine protease activity. These protease complexes activate precursor proteins that contribute to further activation (amplifying the response) or generate inflammatory mediators and cytotoxic elements. There are three main effectors generated during complement activation: C3b, C5a and C5b-9 (also called the membrane attack complex or MAC).

Cellular rejection of transplanted organs can be managed by an array of cellular immune-suppressant drugs that specifically target the cellular immune response. However, a significant population of potential transplant candidates present with donor specific antibodies (DSA) that is often a contraindication for proceeding with transplantation. In addition, de novo anti-donor antibody formation appears to occur in 10-20% of transplanted patients that did not present with high panel reactivity before the transplant. These antibodies bind to the donor organ and initiate an inflammatory response by the host that results in compromised function and ultimately graft loss. Antibody-Mediated Rejection (AMR) is not controlled by standard immune-suppressant drugs and is increasingly recognized as a leading cause of organ rejection. DSA are able to activate the complement system, initially through classical pathway mechanisms, augmented by alternative pathway components that damage the donor organ. In addition, complement activation in the transplant setting has been suggested to occur during the surgical process of transplantation (by ischemia-reperfusion mechanisms). Complement activation products have also been demonstrated to prime and accentuate cellular rejection mechanisms. Thus, complement may contribute to the loss of a transplanted organ in a variety of ways. Factor H, which controls the conversion of C3 to C3a as well as the subsequent generation of C5a, may be effective in limiting organ rejection.

The evidence for a role of complement activation in the pathology of RA is fairly extensive. Studies indicate that complement activation contributes to the pathology of RA. Elevated activation markers in RA patients and the significant protection from disease phenotype that is observed in various rodent models where different complement proteins are absent also suggests an important role for complement in RA etiology. However, work from a number of groups have demonstrated that targeting the complement inhibitor appears to be necessary to show efficacy, and that systemic administration of the un-targeted inhibitor, including FH, was ineffective. In addition, the lack of any genetic association of FH polymorphism with the development of RA appears to further weaken the link with this disease. Surprisingly, as demonstrated herein, FH given systemically does limit the pathology of RA in a mouse model.

Thus, Factor H, as a protein component of the alternative pathway of complement encoded by the complement factor G gene, may be a potential therapeutic for use in preventing or inhibiting allograft rejection and for treating rheumatoid arthritis.

BRIEF SUMMARY OF THE INVENTION

In one aspect, the present invention provides a method for preventing or inhibiting allograft rejection by a recipient of that allograft by treating the recipient with a composition comprising Factor H (FH). In exemplary embodiments, the FH is plasma-derived FH or recombinant FH.

In a further embodiment and in accordance with the above, the recipient is further treated with a first immunosuppressant composition that includes without limitation any one of sirolimus (Rapamycin), FK506 (FK), cyclosporin, and tacrolimus.

In a further embodiment and in accordance with any of the above, the recipient is further treated with a second immunosuppressant composition that is different from the first immunosuppressant composition, where that second immunosuppressant is independently selected from sirolimus (Rapamycin), FK506 (FK), cyclosporin, and tacrolimus.

In a still further embodiment and in accordance with any of the above, the recipient is treated with a composition comprising FH, a composition comprising FK, and a composition comprising Rapamycin.

In a yet further embodiment and in accordance with any of the above, the allograft rejection is an antibody mediated rejection or a combination of antibody and cell mediated rejection.

In a further embodiment and in accordance with any of the above, preventing or inhibiting allograft rejection includes prolonging allograft survival and/or function for a predetermined number of days.

In still further embodiment and in accordance with any of the above, the preventing or inhibiting allograft rejection includes preventing or inhibiting an increase in levels of markers of allograft rejection.

In a still further embodiment and in accordance with any of the above, the allograft rejection being prevented or inhibited is acute antibody-mediated rejection. In such an embodiment, the recipient is treated with FH upon receipt of said allograft until said allograft functions normally. In an exemplary embodiment, normal function of the allograft is determined by recipient creatinine level and/or negative C4d biopsy testing.

In a still further embodiment and in accordance with any of the above, the allograft rejection occurs 3-6 months after receipt of said allograft.

In a still further embodiment and in accordance with any of the above, the allograft comprises an organ. In a further embodiment, the organ is a whole organ. In a still further embodiment, the whole organ is a member selected from kidney, heart, liver, intestine, pancreas and lung.

In a still further embodiment and in accordance with any of the above, the allograft comprises tissue. In a further embodiment, the allograft is selected from a skin graft, a bone graft, a valve, and bone marrow.

In one aspect, the present invention provides a method for treating rheumatoid arthritis in a subject, the method including the step of administering a composition comprising Factor H (FH) to the subject. In exemplary embodiments, the FH is plasma-derived FH or recombinant FH.

In a further embodiment and in accordance with any of the above, the FH is administered to the subject intravenously.

In a still further embodiment and in accordance with any of the above, administering FH results in a reduction of joint inflammation in the subject.

In a yet further embodiment and in accordance with any of the above, administering FH inhibits an initial inflammatory response.

In a further embodiment and in accordance with any of the above, administering FH further promotes resolution of an inflammatory response.

In a still further embodiment and in accordance with any of the above, administering FH results in a reduction of exostosis in the subject.

In a yet further embodiment and in accordance with any of the above, administering FH results in a reduction of damage to cartilage in the subject as compared to a subject that has not received FH.

BRIEF DESCRIPTION OF THE DRAWINGS

FIG. 12 provides a sequence of a Factor H variant of use in the present invention.

DETAILED DESCRIPTION OF THE INVENTION

Overview

Figure 1:
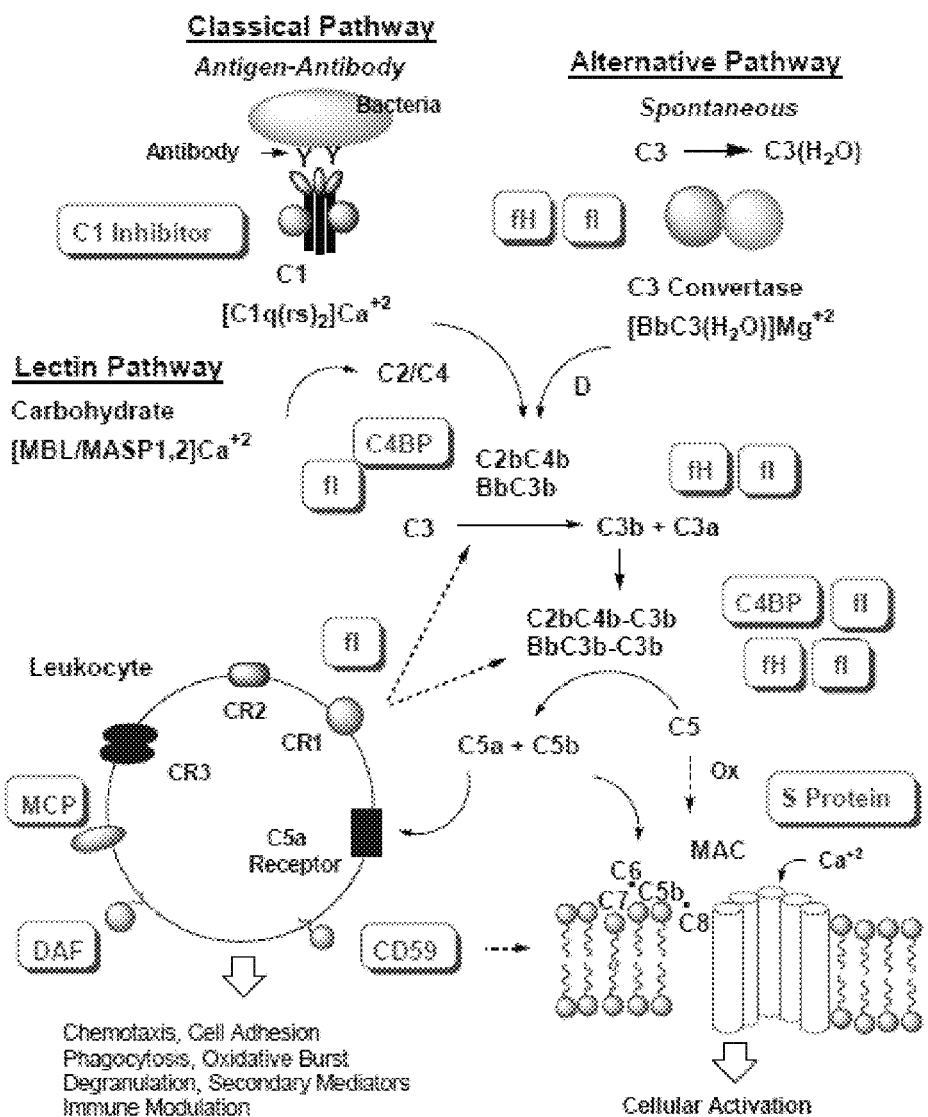
FIG. 1 illustrates the complement cascade. Inhibitor proteins are boxed. fH=factor H; fI=factor I; C4BP=C4 binding protein; DAF=Decay accelerating factor; MCP=Membrane cofactor protein.

The present invention provides methods for preventing or inhibiting allograft rejection and methods for treating rheumatoid arthritis, where such methods include treating a subject in need thereof with a composition that includes Factor H ("FH").

The FH used in treating a subject may be plasma-derived or recombinant Factor H. Plasma-derived FH comprises many variants, as has been described in the literature, and one or a combination of these variants may be used in the methods described herein. A large number of recombinant variants are also described in the literature, and any one or combination of such recombinant FH variants may also be used to prevent or inhibit allograft rejection or to treat rheumatoid arthritis in accordance with the methods described in further detail herein. As will be appreciated, treatment with a combination of both plasma-derived and recombinant FH is also encompassed by the present invention. Treatment with FH may be through subcutaneous administration, intravenous administration, or any other method of administration known in the art.

In one aspect, the present invention provides methods for preventing or inhibiting allograft rejection by a recipient of that allograft by treating that recipient with a composition comprising FH. As is discussed above, treatment with FH may include treatment with one or more variants of FH that are plasma-derived or recombinant. The amount of FH provided may vary, but in general is in a range effective to inhibit complement activation. In further exemplary embodiments, the amount of FH used is in an amount effective to achieve a plasma concentration of about 1-2 mg/ml. In still further embodiments, the amount of FH used for treatment is in a range of 86 mg/kg. The FH may be administered to the recipient of the allograft one or more times after transplantation of the allograft at a range of intervals for a period of days, weeks or months, as is described in further detail herein.

In further embodiments, the recipient of the allograft is also treated with one or more immunosuppressants in addition to FH in order to prevent or inhibit allograft rejection. The one or more immunosuppressants can include without limitation sirolimus (Rapamycin), FK506, cyclosporin, and tacrolimus. Further standard immunosuppressant therapies may also be administered to the recipient in some embodiments, including without limitation mycophenylate mofitil, and steroids. In specific embodiments, the recipient is treated with FH, FK506 and with Rapamycin to prevent or inhibit allograft rejection. Treatment with FH and the one or more immunosuppressants may be accomplished at the same time or at different time points after the receipt of the allograft. In further embodiments, treatment with FH and/or the one or more immunosuppressants is repeated after receipt of the allograft, as is described in further detail herein.

In a further aspect, treatment with FH with or without one or more immunosuppressants is provided just after transplant to prevent or inhibit acute rejection, particularly acute antibody-mediated rejection. In such a method, the treatment is started at the time of transplant of the allograft and continued until the allograft is functioning. For example, in embodiments in which the allograft is a kidney, the treatment would be continued until the recipient shows normal creatinine values and biopsy testing is C4d negative.

In a still further aspect, treatment with FH with or without one or more immunosuppressants is provided to prevent rejection that occurs weeks or months after transplantation. In such situations, the allograft functions normally immediately after transplantation but then deteriorates due to de novo antibody production. Treatment would in this aspect be started when the first signs of rejection manifest and continued until the allograft is again functioning normally.

In exemplary embodiments, treatment with FH with or without one or more immunosuppressants in accordance with the present invention may be used to prevent or inhibit rejection of allografts that include without limitation an organ, a part of an organ or a tissue. In further exemplary embodiments, the allograft may be without limitation kidney, heart, liver, lung, pancreas, intestine, a skin graft, a bone graft, a valve, and bone marrow.

In a further aspect, the present invention provides methods for treating rheumatoid arthritis in a subject by administering a composition comprising FH to that subject. As discussed above, the FH used to treat the subject may comprise one or more variants of FH, and may be plasma-derived or recombinant.

In specific embodiments, the FH administered to the subject reduces joint inflammation in the subject. In further embodiments, the FH administered inhibits an initial inflammatory response and/or promotes the resolution of inflammatory response. In still further embodiments, the FH results in a reduction of exostosis in the subject or in a reduction of damage to the cartilage as compared to a subject that has not received FH.

In further embodiments, the amount of FH administered to the subject is an amount effective to reduce inflammation, exostosis, or damage to cartilage as described above. In still further embodiments and as discussed above for prevention or inhibition of allograft rejection, the amount of FH administered to a subject with rheumatoid arthritis may vary, but in general is in a range effective to inhibit complement activation. In further exemplary embodiments, the amount of FH used is in an amount effective to achieve a plasma concentration of about 1-2 mg/ml. In further embodiments, the amount of FH used for treatment is in a range of 86 mg/kg. The FH may be administered to the subject one or more times at a range of intervals for a period of days, weeks or months, as is described in further detail herein.

Definitions

Unless otherwise specified, the term "Factor H" or "FH" as used herein refers to both plasma-derived and recombinant Factor H and further encompasses one or more variants.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. The term "purified" in some embodiments denotes that a nucleic acid or protein gives rise to essentially one band in an electrophoretic gel. In other embodiments, it means that the nucleic acid or protein is at least 50% pure, more preferably at least 60%, 65%, 70%, 75%, 80%, 85%, 90%, 95%, 96%, 97%, 98%, 99% or more pure. "Purify" or "purification" in other embodiments means removing at least one contaminant from the composition to be purified. In this sense, purification does not require that the purified compound be homogenous, e.g., 100% pure.

As used herein, "administering" (and all grammatical equivalents) includes intravenous administration, intramuscular administration, subcutaneous administration, oral administration, administration as a suppository, topical contact, intraperitoneal, intralesional, or intranasal administration, or the implantation of a slow-release device, e.g., a mini-osmotic pump, to a subject. Administration is by any route including parenteral, and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The terms "therapeutically effective amount or dose" or "therapeutically sufficient amount or dose" or "effective or sufficient amount or dose" or "pharmaceutically effective amount or dose" refer to a dose that produces therapeutic effects for which it is administered. For example, a therapeutically effective amount of a drug useful for treating hemophilia can be the amount that is capable of preventing or relieving one or more symptoms associated with hemophilia. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins, each of which is incorporated herein by reference in its entirety for all purposes and in particular for all teachings related to developing doses and dosing regimens).

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

By "subject" is meant any member of the subphylum chordata, including, without limitation, humans and other primates, including non human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are of interest.

The term "patient," is used in its conventional sense to refer to a living organism suffering from or prone to a condition that can be prevented or treated by administration of a composition of the invention, and includes both humans and non-human species. The terms "patient" and "subject" are used interchangeably throughout the application, and, as discussed above, these terms include both human and veterinary subjects.

As used herein, the term "about" denotes an approximate range of plus or minus 10% from a specified value. For instance, the language "about 20%" encompasses a range of 18-22%.

As used herein, the term "half-life" refers to the period of time it takes for the amount of a substance undergoing decay (or clearance from a sample or from a patient) to decrease by half.

As used herein, the terms "sequence identity" or "% identity", in the context of two or more nucleic acid or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. For sequence comparison, typically one sequence acts as a reference sequence to which test sequences are compared. Optimal alignment of sequences for comparison can be conducted, e.g., by the local homology algorithm of Smith & Waterman, Adv. Appl. Math. 2: 482 (1981); by the homology alignment algorithm of Needleman & Wunsch, J. Mol. Biol. 48: 443 (1970); by the search for similarity method of Pearson & Lipman, Proc. Nat'l. Acad. Sci. USA 85: 2444 (1988); by computerized implementations of these algorithms (GAP, BESTFIT, FASTA, and TFASTA in the Wisconsin Genetics Software Package, Genetics Computer Group, 575 Science Dr., Madison, Wis.); or by visual inspection (see generally, Ausubel, F. M. et al., Current Protocols in Molecular Biology, pub. by Greene Publishing Assoc. and Wiley-Interscience (1987)). One example of an algorithm that is suitable for determining percent sequence identity is the algorithm used in the basic local alignment search tool (hereinafter "BLAST"), see, e.g. Altschul et al., J. Mol. Biol. 215: 403-410 (1990) and Altschul et al., Nucleic Acids Res., 15: 3389-3402 (1997), which is publicly available through the National Center for Biotechnology Information (hereinafter "NCBI").

As used herein, the term "allograft" is used in its conventional sense to refer to a tissue or organ transplanted from a donor to a recipient of the same species but different genetic makeup.

Compositions of the Invention

The methods of the present invention include the use of compositions comprising Factor H. Unless otherwise specified, the term "Factor H" or "FH" as used herein refers to both plasma-derived and recombinant Factor H. Factor H is a protein component of the alternative pathway of complement encoded by the complement factor G gene (for example, CFH; NM000186; GeneID:3075; UniProt ID P08603; Ripoche et al., Biochem. J. 249:593-602 (1988)). Factor H is translated as a 1,213 amino acid precursor polypeptide which is processed by removal of an 18 amino acid signal peptide, resulting in the mature Factor H protein (amino acids 19-1231). As used in the present invention, Factor H encompasses any natural variants, alternative sequences, isoforms or mutant proteins that can be found in a plasma sample, for example a human plasma sample. Examples of Factor H mutations found in the human population include, without limitation, Y402H; V62I; R78G; R127L; Δ224; Q400K; C431S; T493R; C536R; I551T; R567G; C630W; C673S; C673Y; E850K; S890I; H893R; C915S; E936D; Q950H; Y951H; T956M; C959Y; W978C; N997T; V1007I; V1007L; A1010T; T1017I; Y1021F; C1043R; N1050Y; I1059T; Q1076R; R1078S; D1119G; V1134G; Y1142D; Q1143E; W1157R; C1163W; W1183L; W1183R; T1184R; L1189R; S1191L; G1194D; V1197A; E1198A; F1199S; R1210C; R1215G; R1215Q; YPTCAKR1225:1231 FQS; and P1226S. Many of the these mutations have been found to be associated with a variety of diseases and disorders, including, atypical haemolytic uremic syndrome (aHUS), age-related macular degeneration (AMD), membranoproliferative glomulonephritis type II (MPGNII), CFH deficiency, and basal laminar drusen. Factor H also includes proteins containing post-translational modifications. For example, Factor H is believed to be modified by N-acetylglucosamine (GlcNAc) at residues 529, 718, 802, 822, 882, 911, 1029, and 1095.

As will be appreciated, the Factor H used in the methods and compositions described herein may be plasma-derived or recombinant and may further comprise one or more different variants (including full-length and truncated forms).

Variants of plasma-derived Factor H and methods for producing plasma-derived Factor H are known in the art and are described for example in WO 2007/149567; WO2007/066017; WO2008/113589; WO2011/011753; U.S. Pat. No. 7,745,389, each of which is hereby incorporated by reference in its entirety for all purposes and in particular for all teachings related to the production of Factor H, particularly plasma-derived Factor H.

A wide variety of Factor H polymorphisms are known in the art and described for example in WO2000/52479; WO/2006/062716; U.S. Pat. No. 7,351,524; U.S. Pat. No. 7,745,389 (each which is herein incorporated by reference in its entirety for all purposes and in particular for all teachings related to Factor H and variants of Factor H), which also describe recombinant forms of these Factor H polypeptides and methods for producing the same. Many of these variant forms of Factor H are known as "protective" variants that show greater activity in limiting complement activation than plasma-derived Factor H. In non-limiting embodiments, protective variants of Factor H of use in the present invention comprise a sequence in accordance with any of the sequences described in U.S. Pat. No. 7,745,389, including SEQ ID NO:5 of U.S. Pat. No. 7,745,389, which is provided herein as SEQ ID NO: 1 in FIG. 12. In further embodiments, a recombinant Factor H is used in methods and compositions of the invention where that recombinant Factor H has at least 70%, 75%, 80%, 85%, 90%, 91%, 92%, 93%, 94%, 95%, 96%, 97%, 98%, 99% and 100% sequence identity to any of the sequences described in U.S. Pat. No. 7,745,389. In still further embodiments, the recombinant Factor H of use in the present invention has at least 70%, 75%, 80%, 85%, 90%, 91%, 92%, 93%, 94%, 95%, 96%, 97%, 98%, 99% and 100% sequence identity to SEQ ID NO:5 of U.S. Pat. No. 7,745,389, which is provided herein as SEQ ID NO: 1 in FIG. 12. In yet further embodiments, the recombinant Factor H of use in the present invention comprises SEQ ID NO: 1 pictured in FIG. 12 with about 1-100, 3-95, 5-90, 7-85, 9-80, 11-75, 13-70, 15-65, 17-60, 19-55, 21-50, 23-45, 25-40, 27-35 amino acid substitutions.

In addition to compositions comprising Factor H, methods of the invention use compositions comprising immunosuppressants. These immunosuppressants may be included in the same composition as the Factor H, or the immunosuppressants may be provided in separate compositions from Factor H. Such immunosuppressants include without limitation sirolimus (Rapamycin), FK506 (FK), cyclosporin, and tacrolimus.

In certain embodiments, Factor H is provided in a therapeutically effective dose between about 0.05 mg/mL and about 10 mg/mL. In other embodiments, Factor H is present at a concentration of between about 0.1 mg/mL and about 10 mg/mL. In yet other embodiments, Factor H is present at a concentration of between about 0.1 mg/mL and about 5 mg/mL. In another embodiment, Factor H is present at a concentration of between about 0.1 mg/mL and about 2 mg/mL. In another embodiment, Factor H is present at a concentration of between about 1 mg/mL and about 2 mg/mL. In yet other embodiments, Factor H may be present at about 0.01 mg/mL, or at about 0.02 mg/mL, 0.03 mg/mL, 0.04 mg/mL, 0.05 mg/mL, 0.06 mg/mL, 0.07 mg/mL, 0.08 mg/mL, 0.09 mg/mL, 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, 1.0 mg/mL, 1.1 mg/mL, 1.2 mg/mL, 1.3 mg/mL, 1.4 mg/mL, 1.5 mg/mL, 1.6 mg/mL, 1.7 mg/mL, 1.8 mg/mL, 1.9 mg/mL, 2.0 mg/mL, 2.5 mg/mL, 3.0 mg/mL, 3.5 mg/mL, 4.0 mg/mL, 4.5 mg/mL, 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10.0 mg/mL, or a higher concentration. In further embodiments, Factor H is present at a concentration in a range of about 0.1-15, 0.3-14.5, 0.5-14, 0.7-13.5, 0.9-13, 1.1-12.5, 1.3-12, 1.5-11.5, 1.7-11, 1.9-10.5, 2.1-10, 2.3-9.5, 2.5-9, 2.7-8.5, 2.9-8, 3.1-7.5, 3.3-7, 3.5-6.5, 3.7-6, 3.9-5.5, 4.1-5, 4.3-4.5 mg/mL.

In one embodiment, the concentration of a relatively pure Factor H formulation may be determined by spectroscopy (i.e., total protein measured at A280) or other bulk determination (e.g., Bradford assay, silver stain, weight of a lyophilized powder, etc.). In other embodiments, the concentration of Factor H may be determined by a Factor H ELISA assay (e.g., mg/mL antigen).

In still further embodiments, the present invention provides aqueous Factor H compositions comprising a protein concentration of at or about between 10 g/L and 250 g/L. In certain embodiments, the protein concentration of the Factor H composition is at or about between 50 g/L and 200 g/L, or at or about between 70 g/L and 150 g/L, or at or about between 90 g/L and 120 g/L, or at or about between 30 g/L and 70 g/L, or at or about between 40 g/L and 60 g/L or any suitable concentration within these ranges, for example at or about 10 g/L, or at or about 15 g/L, 20 g/L, 25 g/L, 30 g/L, 35 g/L, 40 g/L, 45 g/L, 50 g/L, 55 g/L, 60 g/L, 65 g/L, 70 g/L, 75 g/L, 80 g/L, 85 g/L, 90 g/L, 95 g/L, 100 g/L, 105 g/L, 110 g/L, 115 g/L, 120 g/L, 125 g/L, 130 g/L, 135 g/L, 140 g/L, 145 g/L, 150 g/L, 155 g/L, 160 g/L, 165 g/L, 170 g/L, 175 g/L, 180 g/L, 185 g/L, 190 g/L, 195 g/L, 200 g/L, 205 g/L, 210 g/L, 215 g/L, 220 g/L, 225 g/L, 230 g/L, 235 g/L, 240 g/L, 245 g/L, 250 g/L, or higher. In a preferred embodiment, Factor H compositions having high protein concentrations will also high levels of purity. In one embodiment, at least 90% of the protein in the composition will be Factor H. In a preferred embodiment, at least 95% of the protein in the composition will be Factor H.

In further embodiments, Factor H is provided in a therapeutically effective dose that results in a plasma level concentration in the recipient of about 0.05 mg/mL and about 10 mg/mL. In other embodiments, Factor H is provided in a therapeutically effective dose that results in a plasma level concentration in the recipient of between about 0.1 mg/mL and about 10 mg/mL. In yet other embodiments, Factor H is provided in a therapeutically effective dose that results in a plasma level concentration in the recipient of between about 0.1 mg/mL and about 5 mg/mL. In another embodiment, Factor H is provided in a therapeutically effective dose that results in a plasma level concentration in the recipient of between about 0.1 mg/mL and about 2 mg/mL. In another embodiment, Factor H is provided in a therapeutically effective dose that results in a plasma level concentration in the recipient of between about 1 mg/mL and about 2 mg/mL. In yet other embodiments, Factor H results in a plasma concentration of at about 0.01 mg/mL, or at about 0.02 mg/mL, 0.03 mg/mL, 0.04 mg/mL, 0.05 mg/mL, 0.06 mg/mL, 0.07 mg/mL, 0.08 mg/mL, 0.09 mg/mL, 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, 1.0 mg/mL, 1.1 mg/mL, 1.2 mg/mL, 1.3 mg/mL, 1.4 mg/mL, 1.5 mg/mL, 1.6 mg/mL, 1.7 mg/mL, 1.8 mg/mL, 1.9 mg/mL, 2.0 mg/mL, 2.5 mg/mL, 3.0 mg/mL, 3.5 mg/mL, 4.0 mg/mL, 4.5 mg/mL, 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10.0 mg/mL, or a higher concentration. In further embodiments, Factor H is provided in a therapeutically effective dose that results in a plasma level concentration in the recipient in a range of about 0.1-15, 0.3-14.5, 0.5-14, 0.7-13.5, 0.9-13, 1.1-12.5, 1.3-12, 1.5-11.5, 1.7-11, 1.9-10.5, 2.1-10, 2.3-9.5, 2.5-9, 2.7-8.5, 2.9-8, 3.1-7.5, 3.3-7, 3.5-6.5, 3.7-6, 3.9-5.5, 4.1-5, 4.3-4.5 mg/mL. The plasma level concentration may be determined using standard assays known in the art.

In further embodiments, Factor H is provided in a therapeutically effective dose of about 50-150 mg/kg. In still further embodiments, Factor H is provided in a therapeutically effective dose of about 52-145, 54-140, 56-135, 58-130, 60-125, 62-120, 64-115, 66-110, 68-105, 70-100, 72-95, 74-90, 76-87, 78-86, 80-85 mg/kg. In still further embodiments, Factor H is provided in a therapeutically effective dose of about 70, 70.5, 71, 71.5, 72, 72.5, 73, 73.5, 74, 74.5, 75, 75.5, 76, 76.5, 77, 77.5, 78, 78.5, 79, 79.5, 80, 80.5, 81, 81.5, 82, 82.5, 83, 83.5, 84, 84.5, 85, 85.5, 86, 86.5, 87, 87.5, 88, 88.5, 89, 89.5, 90, 95, 100, 105, 110, 115, 120, 125, 130, 135, 140, 145, 150, 155, 160, 165, 170 mg/kg.

In further embodiments, one or more immunosuppressants (including without limitation sirolimus (Rapamycin), FK506 (FK), cyclosporin, and tacrolimus) is provided in a concentration of about 0.1-10 μM. In further embodiments, the immunosuppressant is provided in a concentration of about 0.1-10, 0.2-9.5, 0.3-9, 0.4-8.5, 0.5-8, 0.6-7.5, 0.7-7, 0.8-6.5, 0.9-6, 1-5.5, 1.1-5, 1.2-4.5, 1.3-4, 1.4-3.5, 1.5-3, 1.6-2.5, 1.7-2 μM. In still further embodiments, the immunosuppressant is provided in a concentration of about 0.1, 0.3, 0.5, 0.7, 0.9, 1.1, 1.3, 1.5, 1.7, 1.9, 2.1, 2.3, 2.5, 2.7, 2.9, 3.1, 3.3, 3.5, 3.7, 3.9, 4.1, 4.3, 4.5, 4.7, 4.9, 5.1, 5.3, 5.5, 5.7, 5.9, 6.1, 6.3, 6.5, 6.7, 6.9, 7.1, 7.3, 7.5, 7.7, 7.9, 8.1, 8.3, 8.5, 8.7, 8.9, 9.1, 9.3, 9.5, 9.7, 9.9, 10.1, 10.3, 10.5, 10.7, 10.9, 11.1, 11.5, 12, 12.5, 13, 13.5, 14, 14.5, and 15 μM.

In still further embodiments, one or more immunosuppressants (including without limitation sirolimus (Rapamycin), FK506 (FK), cyclosporin, and tacrolimus) is provided in a concentration of about 0.1-10 mg/kg. In further embodiments, the immunosuppressant is provided in a concentration of about 0.1-10, 0.2-9.5, 0.3-9, 0.4-8.5, 0.5-8, 0.6-7.5, 0.7-7, 0.8-6.5, 0.9-6, 1-5.5, 1.1-5, 1.2-4.5, 1.3-4, 1.4-3.5, 1.5-3, 1.6-2.5, 1.7-2 mg/kg. In still further embodiments, the immunosuppressant is provided in a concentration of about 0.1, 0.3, 0.5, 0.7, 0.9, 1.1, 1.3, 1.5, 1.7, 1.9, 2.1, 2.3, 2.5, 2.7, 2.9, 3.1, 3.3, 3.5, 3.7, 3.9, 4.1, 4.3, 4.5, 4.7, 4.9, 5.1, 5.3, 5.5, 5.7, 5.9, 6.1, 6.3, 6.5, 6.7, 6.9, 7.1, 7.3, 7.5, 7.7, 7.9, 8.1, 8.3, 8.5, 8.7, 8.9, 9.1, 9.3, 9.5, 9.7, 9.9, 10.1, 10.3, 10.5, 10.7, 10.9, 11.1, 11.5, 12, 12.5, 13, 13.5, 14, 14.5, and 15 mg/kg.

In further embodiments, compositions of use in the methods described herein comprise FK506. In still further embodiments, compositions of use in the methods described herein comprise FK506 in a concentration of about 0.1-10 μM. In further embodiments, FK506 is provided in a concentration of about 0.1-10, 0.2-9.5, 0.3-9, 0.4-8.5, 0.5-8, 0.6-7.5, 0.7-7, 0.8-6.5, 0.9-6, 1-5.5, 1.1-5, 1.2-4.5, 1.3-4, 1.4-3.5, 1.5-3, 1.6-2.5, 1.7-2 μM. In still further embodiments, FK506 is provided in a concentration of about 0.1, 0.3, 0.5, 0.7, 0.9, 1.1, 1.3, 1.5, 1.7, 1.9, 2.1, 2.3, 2.5, 2.7, 2.9, 3.1, 3.3, 3.5, 3.7, 3.9, 4.1, 4.3, 4.5, 4.7, 4.9, 5.1, 5.3, 5.5, 5.7, 5.9, 6.1, 6.3, 6.5, 6.7, 6.9, 7.1, 7.3, 7.5, 7.7, 7.9, 8.1, 8.3, 8.5, 8.7, 8.9, 9.1, 9.3, 9.5, 9.7, 9.9, 10.1, 10.3, 10.5, 10.7, 10.9, 11.1, 11.5, 12, 12.5, 13, 13.5, 14, 14.5, and 15 μM. In still further FK506 is provided in a concentration of about 0.1-10 mg/kg. In further embodiments, the FK506 is provided in a concentration of about 0.1-10, 0.2-9.5, 0.3-9, 0.4-8.5, 0.5-8, 0.6-7.5, 0.7-7, 0.8-6.5, 0.9-6, 1-5.5, 1.1-5, 1.2-4.5, 1.3-4, 1.4-3.5, 1.5-3, 1.6-2.5, 1.7-2 mg/kg. In still further embodiments, the FK506 is provided in a concentration of about 0.1, 0.3, 0.5, 0.7, 0.9, 1.1, 1.3, 1.5, 1.7, 1.9, 2.1, 2.3, 2.5, 2.7, 2.9, 3.1, 3.3, 3.5, 3.7, 3.9, 4.1, 4.3, 4.5, 4.7, 4.9, 5.1, 5.3, 5.5, 5.7, 5.9, 6.1, 6.3, 6.5, 6.7, 6.9, 7.1, 7.3, 7.5, 7.7, 7.9, 8.1, 8.3, 8.5, 8.7, 8.9, 9.1, 9.3, 9.5, 9.7, 9.9, 10.1, 10.3, 10.5, 10.7, 10.9, 11.1, 11.5, 12, 12.5, 13, 13.5, 14, 14.5, and 15 mg/kg. In still further embodiments, FK506 is provided in a concentration of about 1-30, 3.5-29.5, 4-29, 4.5-28.5, 5-28, 5.5-27.5, 6-27, 6.5-26.5, 7-26, 7.5-25.5, 8-25, 8.5-24.5, 9-24, 9.5-23.5, 10-23, 10.5-22.5, 11-22, 11.5-21.5, 12-21, 12.5-20.5, 13-20, 13.5-19.5, 14-19, 14.5-18.5, 15-18, 15.5-, 7.5, 16-17, 2-4, 2.5-3.5, 3-3.5 mg/kg. In yet further embodiments, FK506 is provided in a concentration of about 1, 1.2, 1.4, 1.6, 1.8, 2, 2.2, 2.4, 2.6, 2.8, 3, 3.2, 3.4, 3.6, 3.8, 4, 4.2, 4.4, 4.6, 4.8, 5, 5.2, 5.4, 5.6, 5.8, 6, 6.2, 6.4, 6.6, 6.8, 7, 7.2, 7.4, 7.6, 7.8, 8, 8.2, 8.4, 8.6, 8.8, 9, 9.2, 9.4, 9.6, 9.8, 10, 10.2, 10.4, 10.6, 10.8, 11, 11.2, 11.4, 11.6, 11.8, 12 mg/kg.

In further embodiments, compositions of use in the methods described herein comprise Rapamycin. In still further embodiments, compositions of use in the methods described herein comprise Rapamycin a concentration of about 0.1-10 μM. In further embodiments, Rapamycin is provided in a concentration of about 0.1-10, 0.2-9.5, 0.3-9, 0.4-8.5, 0.5-8, 0.6-7.5, 0.7-7, 0.8-6.5, 0.9-6, 1-5.5, 1.1-5, 1.2-4.5, 1.3-4, 1.4-3.5, 1.5-3, 1.6-2.5, 1.7-2 μM. In still further embodiments, Rapamycin is provided in a concentration of about 0.1, 0.3, 0.5, 0.7, 0.9, 1.1, 1.3, 1.5, 1.7, 1.9, 2.1, 2.3, 2.5, 2.7, 2.9, 3.1, 3.3, 3.5, 3.7, 3.9, 4.1, 4.3, 4.5, 4.7, 4.9, 5.1, 5.3, 5.5, 5.7, 5.9, 6.1, 6.3, 6.5, 6.7, 6.9, 7.1, 7.3, 7.5, 7.7, 7.9, 8.1, 8.3, 8.5, 8.7, 8.9, 9.1, 9.3, 9.5, 9.7, 9.9, 10.1, 10.3, 10.5, 10.7, 10.9, 11.1, 11.5, 12, 12.5, 13, 13.5, 14, 14.5, and 15 μM. In still further embodiments, Rapamycin is provided in a concentration of about 0.1-10 mg/kg. In yet further embodiments, Rapamycin is provided in a concentration of about 0.1-10, 0.2-9.5, 0.3-9, 0.4-8.5, 0.5-8, 0.6-7.5, 0.7-7, 0.8-6.5, 0.9-6, 1-5.5, 1.1-5, 1.2-4.5, 1.3-4, 1.4-3.5, 1.5-3, 1.6-2.5, 1.7-2, 0.1-0.9, 0.2-0.8, 0.3-0.7, 0.4-0.6 mg/kg. In still further embodiments, Rapamycin is provided in a concentration of about 0.1, 0.3, 0.5, 0.7, 0.9, 1.1, 1.3, 1.5, 1.7, 1.9, 2.1, 2.3, 2.5, 2.7, 2.9, 3.1, 3.3, 3.5, 3.7, 3.9, 4.1, 4.3, 4.5, 4.7, 4.9, 5.1, 5.3, 5.5, 5.7, 5.9, 6.1, 6.3, 6.5, 6.7, 6.9, 7.1, 7.3, 7.5, 7.7, 7.9, 8.1, 8.3, 8.5, 8.7, 8.9, 9.1, 9.3, 9.5, 9.7, 9.9, 10.1, 10.3, 10.5, 10.7, 10.9, 11.1, 11.5, 12, 12.5, 13, 13.5, 14, 14.5, and 15 mg/kg.

The Factor H and immunosuppressant compositions in further embodiments have very high levels of purity. In one embodiment, at least 90% of the total protein in a composition provided herein will be Factor H or the immunosuppressant. In a preferred embodiment, at least 95% of the total protein in a composition provided herein will be Factor H or the immunosuppressant. In other embodiments, at least 90%, 91%, 92%, 93%, 94%, 95%, 96%, 97%, 98%, 99%, 99.5%, or more of the total protein of the composition will be Factor H or the immunosuppressant. In one preferred embodiment, at least 96% of the total protein of the composition will be Factor H or the immunosuppressant. In a preferred embodiment, at least 97% of the total protein of the composition will be Factor H or the immunosuppressant. In another preferred embodiment, at least 98% of the total protein of the composition will be Factor H or the immunosuppressant. In another preferred embodiment, at least 99% of the total protein of the composition will be Factor H or the immunosuppressant.

In some embodiments, the compositions described herein will have osmolarities that are comparable to physiologic osmolarity, about 285 to 295 mOsmol/kg (Lacy et al., *Drug Information Handbook—Lexi-Comp* 1999:1254). In certain embodiments, the osmolarity of the formulation will be at or about between 200 and 350 mOsmol/kg, preferably at or about between 240 and 300 mOsmol/kg. In particular embodiments, the osmolarity of the formulation will be at or about 200 mOsmol/kg, or 210 mOsmol/kg, 220 mOsmol/kg, 230 mOsmol/kg, 240 mOsmol/kg, 245 mOsmol/kg, 250 mOsmol/kg, 255 mOsmol/kg, 260 mOsmol/kg, 265 mOsmol/kg, 270 mOsmol/kg, 275 mOsmol/kg, 280 mOsmol/kg, 285 mOsmol/kg, 290 mOsmol/kg, 295 mOsmol/kg, 300 mOsmol/kg, 310 mOsmol/kg, 320 mOsmol/kg, 330 mOsmol/kg, 340 mOsmol/kg, 340 mOsmol/kg, or 350 mOsmol/kg. In yet other embodiments, the osmolarity of the formulation will be higher, for example at or about between 200 and 1000 mOsmol/kg, or at or about 400 mOsmol/kg, 450 mOsmol/kg, 500 mOsmol/kg, 550 mOsmol/kg, 600 mOsmol/kg, 650 mOsmol/kg, 700 mOsmol/kg, 750 mOsmol/kg, 800 mOsmol/kg, 850 mOsmol/kg, 900 mOsmol/kg, 950 mOsmol/kg, 1000 mOsmol/kg, or higher.

The compositions discussed herein are generally stable in liquid form for an extended period of time. In certain embodiments, the formulations are stable for at least at or about 3 months at room temperature, or at least at or about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 months or more at room temperature. The composition will also generally be stable for at least at or about 18 months under refrigerated conditions (typically between about 2° C. and about 8° C.), or for at least at or about 21, 24, 27, 30, 33, 36, 39, 42, 45, 48, 51, 54, 57, 60 months or more under refrigerated conditions.

In other embodiments, the compositions discussed herein are generally stable in lyophilized form for an extended period of time. In certain embodiments, the formulations are stable for at least at or about 3 months at room temperature, or at least at or about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 months at room temperature. The formulation will also generally be stable for at least at or about 18 months under refrigerated conditions (typically between about 2° C. and about 8° C.), or for at least at or about 21, 24, 27, 30, 33, 36, 39, 42, 45, 48, 51, 54, 57, or 60 months under refrigerated conditions.

Methods of Preventing or Inhibiting Allograft Rejection

In one aspect, the present invention provides methods for preventing or inhibiting allograft rejection by a recipient of that allograft by treating that recipient with a composition comprising FH. As is discussed above, treatment with FH may include treatment with one or more variants of FH that are plasma-derived or recombinant.

Prevention of allograft rejection is of particular importance, as rejection of an allograft can have serious consequences for the recipient. Thus, treatment to prevent rejection or inhibit the progress of rejection is a primary concern in the field of organ transplantation.

The methods of the present invention can be used to prevent or inhibit the rejection of any allograft, including any whole or portion of an organ or tissue. In exemplary and non-limiting embodiments, the methods described herein for preventing or inhibiting allograft rejection can be used for allografts such as kidney, heart, liver, intestine, pancreas, lung, skin graft, bone graft, valve, and bone marrow.

In further aspects, the recipient of the allograft is also treated with one or more immunosuppressants in addition to FH in order to prevent or inhibit allograft rejection. The one or more immunosuppressants can include without limitation sirolimus (Rapamycin), FK506, cyclosporin, and tacrolimus. In specific embodiments, the recipient is treated with FH, FK506 and with Rapamycin to prevent or inhibit allograft rejection. Treatment with FH and the one or more immunosuppressants may be accomplished at the same time or at different time points after receipt of the allograft. In further embodiments, treatment with FH and/or the one or more immunosuppressants is repeated periodically for a period of time after receipt of the allograft, as is described in further detail herein.

In further embodiments, treatment with FH with or without one or more immunosuppressants in accordance with the present invention may be used to prevent or inhibit rejection of allografts that include without limitation an organ, a part of an organ or a tissue. In further exemplary embodiments, the allograft may be without limitation kidney, heart, liver, lung, pancreas, intestine, a skin graft, a bone graft, a valve, and bone marrow.

In some aspects, the Factor H and/or immunosuppressant compositions of the invention can be administered to the recipient by intravenous, intraocular, subcutaneous, and/or intramuscular means. In further aspects, the Factor H and/or immunosuppressant compositions herein can be administered either systemically or locally. Systemic administration includes without limitation oral, transdermal, subdermal, intraperitoneal, intravenous, subcutaneous, transnasal, sublingual, or rectal. Local administration may include without limitation administration directly to the allograft before and/or after transplantation via perfusion, injection, or other contact with the allograft, or by administration at the site of transplantation (before and/or after transplantation), or delivery via a sustained delivery device implanted at or near the transplant site.

In certain embodiments, the methods of the present invention prevent or inhibit antibody mediated rejection (AMR). In further embodiments, the methods of the present invention prevent or inhibit cell mediated rejection (CMR). In still further embodiments, methods of the present invention prevent or inhibit a combination of antibody and cell mediated rejection.

In a further aspect, treatment with FH with or without one or more immunosuppressants is provided just after transplant to prevent or inhibit acute rejection, particularly acute antibody-mediated rejection. In such a method, the treatment is started at the time of transplant of the allograft and continued until the allograft is functioning normally. Methods for determining whether the allograft is functioning normally will depend on the organ or tissue being transplanted and such assays of normal function are well known in the art for particular organs. For example, in embodiments in which the allograft is a kidney, the treatment would be continued until the recipient shows normal creatinine values and biopsy testing is C4d negative.

In a still further aspect, treatment with FH with or without one or more immunosuppressants is provided to prevent or inhibit a delayed rejection that occurs weeks or months after transplantation. In such situations, the allograft functions normally immediately after transplantation but then deteriorates due to de novo antibody production. Treatment would in this aspect be started when the first signs of rejection manifest and continued until the allograft is again functioning normally. Again, methods for determining whether the allograft is functioning will depend on the organ or tissue being transplanted and are well known in the art. For example, in embodiments in which the allograft is a kidney, the treatment would be continued until the recipient shows normal creatinine values and biopsy testing is C4d negative.

For any of the methods for preventing or inhibiting allograft rejection discussed herein, the Factor H discussed may be plasma-derived or recombinant and may further comprise one or more different variants (including full-length and truncated forms). In exemplary embodiments, the Factor H used in methods for preventing or inhibiting allograft rejection include recombinant protective variants of Factor H that comprise a sequence in accordance with any of the sequences described in U.S. Pat. No. 7,745,389, including SEQ ID NO:5 of U.S. Pat. No. 7,745,389, which is provided herein as SEQ ID NO: 1 in FIG. 12. In further embodiments, a recombinant Factor H is used in methods and compositions of the invention where that recombinant Factor H has at least 70%, 75%, 80%, 85%, 90%, 91%, 92%, 93%, 94%, 95%, 96%, 97%, 98%, 99% and 100% sequence identity to any of the sequences described in U.S. Pat. No. 7,745,389. In still further embodiments, the recombinant Factor H of use in the present invention has at least 70%, 75%, 80%, 85%, 90%, 91%, 92%, 93%, 94%, 95%, 96%, 97%, 98%, 99% and 100% sequence identity to SEQ ID NO:5 of U.S. Pat. No. 7,745,389, which is provided herein as SEQ ID NO: 1 in FIG. 12. In yet further embodiments, the recombinant Factor H of use in the present invention comprises SEQ ID NO: 1 pictured in FIG. 12 with about 1-100, 3-95, 5-90, 7-85, 9-80, 11-75, 13-70, 15-65, 17-60, 19-55, 21-50, 23-45, 25-40, 27-35 amino acid substitutions. The following discussion of treatment methods utilizing Factor H encompasses plasma derived or recombinant Factor H, including variants thereof, such as one or more of the protective variants discussed herein.

The amount of FH provided to the recipient may vary, but in general is in a range effective to inhibit complement activation. Complement inhibition can be evaluated based on any methods known in the art, including for example, in vitro zymosan assays, assays for lysis of erythrocytes, immune complex activation assays, and mannan activation assays. In some embodiments, the CR2-FH has one or more of the following properties of FH: (1) binding to C-reactive protein (CRP), (2) binding to C3b, (3) binding to heparin, (4) binding to sialic acid, (5) binding to endothelial cell surfaces, (6) binding to cellular integrin receptor, (7) binding to pathogens, (8) C3b co-factor activity, (9) C3b decay-acceleration activity, and (10) inhibiting the alternative complement pathway.

In further exemplary embodiments, the amount of FH used is in an amount effective to achieve a plasma concentration of about 1-2 mg/ml. In still further embodiments, the amount of FH used for treatment is in a range of 86 mg/kg. The FH may be administered to the recipient of the allograft one or more times after transplantation of the allograft at a range of intervals for a period of days, weeks or months, as is described in further detail herein.

In embodiments in which one or more immunosuppressants are provided to the recipient, the amount of the one or more immunosuppressants may also vary, but in general is in a range effective to inhibit allograft rejection. In further exemplary embodiments, the amount of immunosuppressants used is in an amount of about 0.1-10 mg/kg. The one or more immunosuppressants may be administered to the recipient of the allograft one or more times after transplantation of the allograft at a range of intervals for a period of days, weeks or months, as is described in further detail herein.

In accordance with any of the above, the FH provided to the recipient to prevent allograft rejection is provided in a therapeutically effective dose between about 0.05 mg/mL and about 10 mg/mL. In other embodiments, Factor H is present at a concentration of between about 0.1 mg/mL and about 10 mg/mL. In yet other embodiments, Factor H is present at a concentration of between about 0.1 mg/mL and about 5 mg/mL. In another embodiment, Factor H is present at a concentration of between about 0.1 mg/mL and about 2 mg/mL. In another embodiment, Factor H is present at a concentration of between about 1 mg/mL and about 2 mg/mL. In yet other embodiments, Factor H may be present at about 0.01 mg/mL, or at about 0.02 mg/mL, 0.03 mg/mL, 0.04 mg/mL, 0.05 mg/mL, 0.06 mg/mL, 0.07 mg/mL, 0.08 mg/mL, 0.09 mg/mL, 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, 1.0 mg/mL, 1.1 mg/mL, 1.2 mg/mL, 1.3 mg/mL, 1.4 mg/mL, 1.5 mg/mL, 1.6 mg/mL, 1.7 mg/mL, 1.8 mg/mL, 1.9 mg/mL, 2.0 mg/mL, 2.5 mg/mL, 3.0 mg/mL, 3.5 mg/mL, 4.0 mg/mL, 4.5 mg/mL, 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10.0 mg/mL, or a higher concentration. In further embodiments, Factor H is present at a concentration in a range of about 0.1-15, 0.3-14.5, 0.5-14, 0.7-13.5, 0.9-13, 1.1-12.5, 1.3-12, 1.5-11.5, 1.7-11, 1.9-10.5, 2.1-10, 2.3-9.5, 2.5-9, 2.7-8.5, 2.9-8, 3.1-7.5, 3.3-7, 3.5-6.5, 3.7-6, 3.9-5.5, 4.1-5, 4.3-4.5 mg/mL.

In one embodiment, the concentration of a relatively pure Factor H formulation may be determined by spectroscopy (i.e., total protein measured at A280) or other bulk determination (e.g., Bradford assay, silver stain, weight of a lyophilized powder, etc.). In other embodiments, the concentration of Factor H may be determined by a Factor H ELISA assay (e.g., mg/mL antigen).

In still further embodiments, the present invention provides aqueous Factor H compositions comprising a protein concentration of at or about between 10 g/L and 250 g/L. In certain embodiments, the protein concentration of the Factor H composition is at or about between 50 g/L and 200 g/L, or at or about between 70 g/L and 150 g/L, or at or about between 90 g/L and 120 g/L, or at or about between 30 g/L and 70 g/L, or at or about between 40 g/L and 60 g/L or any suitable concentration within these ranges, for example at or about 10 g/L, or at or about 15 g/L, 20 g/L, 25 g/L, 30 g/L, 35 g/L, 40 g/L, 45 g/L, 50 g/L, 55 g/L, 60 g/L, 65 g/L, 70 g/L, 75 g/L, 80 g/L, 85 g/L, 90 g/L, 95 g/L, 100 g/L, 105 g/L, 110 g/L, 115 g/L, 120 g/L, 125 g/L, 130 g/L, 135 g/L, 140 g/L, 145 g/L, 150 g/L, 155 g/L, 160 g/L, 165 g/L, 170 g/L, 175 g/L, 180 g/L, 185 g/L, 190 g/L, 195 g/L, 200 g/L, 205 g/L, 210 g/L, 215 g/L, 220 g/L, 225 g/L, 230 g/L, 235 g/L, 240 g/L, 245 g/L, 250 g/L, or higher. In a preferred embodiment, Factor H compositions having high protein concentrations will also high levels of purity. In one embodiment, at least 90% of the protein in the composition will be Factor H. In a preferred embodiment, at least 95% of the protein in the composition will be Factor H.

In further embodiments, Factor H is provided in a therapeutically effective dose that results in a plasma level concentration in the recipient of about 0.05 mg/mL and about 10 mg/mL. In other embodiments, Factor H is provided in a therapeutically effective dose that results in a plasma level concentration in the recipient of between about 0.1 mg/mL and about 10 mg/mL. In yet other embodiments, Factor H is provided in a therapeutically effective dose that results in a plasma level concentration in the recipient of between about 0.1 mg/mL and about 5 mg/mL. In another embodiment, Factor H is provided in a therapeutically effective dose that results in a plasma level concentration in the recipient of between about 0.1 mg/mL and about 2 mg/mL. In another embodiment, Factor H is provided in a therapeutically effective dose that results in a plasma level concentration in the recipient of between about 1 mg/mL and about 2 mg/mL. In yet other embodiments, Factor H results in a plasma concentration of at about 0.01 mg/mL, or at about 0.02 mg/mL, 0.03 mg/mL, 0.04 mg/mL, 0.05 mg/mL, 0.06 mg/mL, 0.07 mg/mL, 0.08 mg/mL, 0.09 mg/mL, 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, 1.0 mg/mL, 1.1 mg/mL, 1.2 mg/mL, 1.3 mg/mL, 1.4 mg/mL, 1.5 mg/mL, 1.6 mg/mL, 1.7 mg/mL, 1.8 mg/mL, 1.9 mg/mL, 2.0 mg/mL, 2.5 mg/mL, 3.0 mg/mL, 3.5 mg/mL, 4.0 mg/mL, 4.5 mg/mL, 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10.0 mg/mL, or a higher concentration. In further embodiments, Factor H is provided in a therapeutically effective dose that results in a plasma level concentration in the recipient in a range of about 0.1-15, 0.3-14.5, 0.5-14, 0.7-13.5, 0.9-13, 1.1-12.5, 1.3-12, 1.5-11.5, 1.7-11, 1.9-10.5, 2.1-10, 2.3-9.5, 2.5-9, 2.7-8.5, 2.9-8, 3.1-7.5, 3.3-7, 3.5-6.5, 3.7-6, 3.9-5.5, 4.1-5, 4.3-4.5 mg/mL. The plasma level concentration may be determined using standard assays known in the art.

In further embodiments, Factor H is provided in a therapeutically effective dose of about 50-150 mg/kg. In still further embodiments, Factor H is provided in a therapeutically effective dose of about 52-145, 54-140, 56-135, 58-130, 60-125, 62-120, 64-115, 66-110, 68-105, 70-100, 72-95, 74-90, 76-87, 78-86, 80-85 mg/kg. In still further embodiments, Factor H is provided in a therapeutically effective dose of about 70, 70.5, 71, 71.5, 72, 72.5, 73, 73.5, 74, 74.5, 75, 75.5, 76, 76.5, 77, 77.5, 78, 78.5, 79, 79.5, 80, 80.5, 81, 81.5, 82, 82.5, 83, 83.5, 84, 84.5, 85, 85.5, 86, 86.5, 87, 87.5, 88, 88.5, 89, 89.5, 90 mg/kg.

In further embodiments, the present invention provides methods of preventing or inhibiting allograft rejection by administering both Factor H and one or more immunosuppressants to the recipient. The FH and the one or more immunosuppressants may be administered to the recipient at the same time or at different time points before and/or after transplantation. The FH and the one or more immunosuppressants may further be administered in the same composition or as different compositions. As will be appreciated, any of the concentration and dose amounts and ranges discussed above for FH can be provided to the recipient in any combination with any of the concentration and dose amounts and ranges described herein for the one or more immunosuppressants.

In further embodiments and in accordance with any of the above, the one or more immunosuppressants (including without limitation sirolimus (Rapamycin), FK506 (FK), cyclosporin, and tacrolimus) is provided in a concentration of about 0.1-10 µM. In further embodiments, the immunosuppressant is provided in a concentration of about 0.1-10, 0.2-9.5, 0.3-9, 0.4-8.5, 0.5-8, 0.6-7.5, 0.7-7, 0.8-6.5, 0.9-6, 1-5.5, 1.1-5, 1.2-4.5, 1.3-4, 1.4-3.5, 1.5-3, 1.6-2.5, 1.7-2 µM. In still further embodiments, the immunosuppressant is provided in a concentration of about 0.1, 0.3, 0.5, 0.7, 0.9, 1.1, 1.3, 1.5, 1.7, 1.9, 2.1, 2.3, 2.5, 2.7, 2.9, 3.1, 3.3, 3.5, 3.7, 3.9, 4.1, 4.3, 4.5, 4.7, 4.9, 5.1, 5.3, 5.5, 5.7, 5.9, 6.1, 6.3, 6.5, 6.7, 6.9, 7.1, 7.3, 7.5, 7.7, 7.9, 8.1, 8.3, 8.5, 8.7, 8.9, 9.1, 9.3, 9.5, 9.7, 9.9, 10.1, 10.3, 10.5, 10.7, 10.9, 11.1, 11.5, 12, 12.5, 13, 13.5, 14, 14.5, and 15 µM.

In still further embodiments, one or more immunosuppressants (including without limitation sirolimus (Rapamycin), FK506 (FK), cyclosporin, and tacrolimus) is provided to the recipient in a concentration of about 0.1-10 mg/kg. In further embodiments, the immunosuppressant is provided in a concentration of about 0.1-10, 0.2-9.5, 0.3-9, 0.4-8.5, 0.5-8, 0.6-7.5, 0.7-7, 0.8-6.5, 0.9-6, 1-5.5, 1.1-5, 1.2-4.5, 1.3-4, 1.4-3.5, 1.5-3, 1.6-2.5, 1.7-2 mg/kg. In still further embodiments, the immunosuppressant is provided in a concentration of about 0.1, 0.3, 0.5, 0.7, 0.9, 1.1, 1.3, 1.5, 1.7, 1.9, 2.1, 2.3, 2.5, 2.7, 2.9, 3.1, 3.3, 3.5, 3.7, 3.9, 4.1, 4.3, 4.5, 4.7, 4.9, 5.1, 5.3, 5.5, 5.7, 5.9, 6.1, 6.3, 6.5, 6.7, 6.9, 7.1, 7.3, 7.5, 7.7, 7.9, 8.1, 8.3, 8.5, 8.7, 8.9, 9.1, 9.3, 9.5, 9.7, 9.9, 10.1, 10.3, 10.5, 10.7, 10.9, 11.1, 11.5, 12, 12.5, 13, 13.5, 14, 14.5, and 15 mg/kg.

In yet further embodiments FK506 is administered to the recipient in addition to FH to prevent or inhibit allograft rejection. In still further embodiments, FK506 is administered to the recipient in a concentration of about 0.1-10 µM. In further embodiments, FK506 is provided in a concentration of about 0.1-10, 0.2-9.5, 0.3-9, 0.4-8.5, 0.5-8, 0.6-7.5, 0.7-7, 0.8-6.5, 0.9-6, 1-5.5, 1.1-5, 1.2-4.5, 1.3-4, 1.4-3.5, 1.5-3, 1.6-2.5, 1.7-2 µM. In still further embodiments, FK506 is provided in a concentration of about 0.1, 0.3, 0.5, 0.7, 0.9, 1.1, 1.3, 1.5, 1.7, 1.9, 2.1, 2.3, 2.5, 2.7, 2.9, 3.1, 3.3, 3.5, 3.7, 3.9, 4.1, 4.3, 4.5, 4.7, 4.9, 5.1, 5.3, 5.5, 5.7, 5.9, 6.1, 6.3, 6.5, 6.7, 6.9, 7.1, 7.3, 7.5, 7.7, 7.9, 8.1, 8.3, 8.5, 8.7, 8.9, 9.1, 9.3, 9.5, 9.7, 9.9, 10.1, 10.3, 10.5, 10.7, 10.9, 11.1, 11.5, 12, 12.5, 13, 13.5, 14, 14.5, and 15 µM. In still further FK506 is provided in a concentration of about 0.1-10 mg/kg. In further embodiments, the FK506 is provided in a concentration of about 0.1-10, 0.2-9.5, 0.3-9, 0.4-8.5, 0.5-8, 0.6-7.5, 0.7-7, 0.8-6.5, 0.9-6, 1-5.5, 1.1-5, 1.2-4.5, 1.3-4, 1.4-3.5, 1.5-3, 1.6-2.5, 1.7-2 mg/kg. In still further embodiments, the FK506 is provided in a concentration of about 0.1, 0.3, 0.5, 0.7, 0.9, 1.1, 1.3, 1.5, 1.7, 1.9, 2.1, 2.3, 2.5, 2.7, 2.9, 3.1, 3.3, 3.5, 3.7, 3.9, 4.1, 4.3, 4.5, 4.7, 4.9, 5.1, 5.3, 5.5, 5.7, 5.9, 6.1, 6.3, 6.5, 6.7, 6.9, 7.1, 7.3, 7.5, 7.7, 7.9, 8.1, 8.3, 8.5, 8.7, 8.9, 9.1, 9.3, 9.5, 9.7, 9.9, 10.1, 10.3, 10.5, 10.7, 10.9, 11.1, 11.5, 12, 12.5, 13, 13.5, 14, 14.5, and 15 mg/kg. In still further embodiments, FK506 is provided in a concentration of about 1-30, 3.5-29.5, 4-29, 4.5-28.5, 5-28, 5.5-27.5, 6-27, 6.5-26.5, 7-26, 7.5-25.5, 8-25, 8.5-24.5, 9-24, 9.5-23.5, 10-23, 10.5-22.5, 11-22, 11.5-21.5, 12-21, 12.5-20.5, 13-20, 13.5-19.5, 14-19, 14.5-18.5, 15-18, 15.5-, 7.5, 16-17, 2-4, 2.5-3.5, 3-3.5 mg/kg. In yet further embodiments, FK506 is provided in a concentration of about 1, 1.2, 1.4, 1.6, 1.8, 2, 2.2, 2.4, 2.6, 2.8, 3, 3.2, 3.4, 3.6, 3.8, 4, 4.2, 4.4, 4.6, 4.8, 5, 5.2, 5.4, 5.6, 5.8, 6, 6.2, 6.4, 6.6, 6.8, 7, 7.2, 7.4, 7.6, 7.8, 8, 8.2, 8.4, 8.6, 8.8, 9, 9.2, 9.4, 9.6, 9.8, 10, 10.2, 10.4, 10.6, 10.8, 11, 11.2, 11.4, 11.6, 11.8, 12 mg/kg.

In yet further embodiments Rapamycin is administered to the recipient in addition to FH to prevent or inhibit allograft rejection. In still further embodiments, Rapamycin is administered to the recipient in a concentration of about 0.1-10 µM. In further embodiments, Rapamycin is provided in a concentration of about 0.1-10, 0.2-9.5, 0.3-9, 0.4-8.5, 0.5-8, 0.6-7.5, 0.7-7, 0.8-6.5, 0.9-6, 1-5.5, 1.1-5, 1.2-4.5, 1.3-4, 1.4-3.5, 1.5-3, 1.6-2.5, 1.7-2 µM. In still further embodiments, Rapamycin is provided in a concentration of about 0.1, 0.3, 0.5, 0.7, 0.9, 1.1, 1.3, 1.5, 1.7, 1.9, 2.1, 2.3, 2.5, 2.7, 2.9, 3.1, 3.3, 3.5, 3.7, 3.9, 4.1, 4.3, 4.5, 4.7, 4.9, 5.1, 5.3, 5.5, 5.7, 5.9, 6.1, 6.3, 6.5, 6.7, 6.9, 7.1, 7.3, 7.5, 7.7, 7.9, 8.1, 8.3, 8.5, 8.7, 8.9, 9.1, 9.3, 9.5, 9.7, 9.9, 10.1, 10.3, 10.5, 10.7, 10.9, 11.1, 11.5, 12, 12.5, 13, 13.5, 14, 14.5, and 15 µM. In still further embodiments, Rapamycin is provided in a concentration of about 0.1-10 mg/kg. In yet further embodiments, Rapamycin is provided in a concentration of about 0.1-10, 0.2-9.5, 0.3-9, 0.4-8.5, 0.5-8, 0.6-7.5, 0.7-7, 0.8-6.5, 0.9-6, 1-5.5, 1.1-5, 1.2-4.5, 1.3-4, 1.4-3.5, 1.5-3, 1.6-2.5, 1.7-2, 0.1-0.9, 0.2-0.8, 0.3-0.7, 0.4-0.6 mg/kg. In still further embodiments, Rapamycin is provided in a concentration of about 0.1, 0.3, 0.5, 0.7, 0.9, 1.1, 1.3, 1.5, 1.7, 1.9, 2.1, 2.3, 2.5, 2.7, 2.9, 3.1, 3.3, 3.5, 3.7, 3.9, 4.1, 4.3, 4.5, 4.7, 4.9, 5.1, 5.3, 5.5, 5.7, 5.9, 6.1, 6.3, 6.5, 6.7, 6.9, 7.1, 7.3, 7.5, 7.7, 7.9, 8.1, 8.3, 8.5, 8.7, 8.9, 9.1, 9.3, 9.5, 9.7, 9.9, 10.1, 10.3, 10.5, 10.7, 10.9, 11.1, 11.5, 12, 12.5, 13, 13.5, 14, 14.5, and 15 mg/kg.

In further embodiments and in accordance with any of the above, the present invention provides methods of preventing or inhibiting allograft rejection by treating the recipient with Factor H, FK506, and Rapamycin. In further embodiments, this combination therapy is provided in which the concentrations of Factor H, FK506, and Rapamycin are in any combination of the above described combinations. In exemplary embodiments, Factor H is provided in a therapeutically effective dose between about 0.05 mg/mL and about 10 mg/mL and FK506 and Rapamycin are provided in doses as listed as Variants 1-20 in Table A. As will be appreciated, the Factor H, FK506, and Rapamycin can be provided in the same composition or in separate compositions to the recipient and may also be administered to the recipient at the same time or at different time points before and/or after transplantation.

In still further embodiments, Factor H is provided in a therapeutically effective dose that results in a plasma level concentration in the recipient of ranges of 0.1-10, 1-9, 2-8, 3-7, 4-6, 1-2 mg/mL, and FK506 and Rapamycin are provided in doses as listed as Variations 1-20 in Table A. As discussed above, Factor H, FK506, and Rapamycin can be provided in the same composition or in separate compositions to the recipient and may also be administered to the recipient at the same time or at different time points before and/or after transplantation.

In yet further embodiments, Factor H is provided in a range of about 50-150 mg/kg and FK506 and Rapamycin are provided in doses as listed as Variation 1-20 in Table A. In still further embodiments, Factor H is provided is a dose of about 70, 70.5, 71, 71.5, 72, 72.5, 73, 73.5, 74, 74.5, 75, 75.5, 76, 76.5, 77, 77.5, 78, 78.5, 79, 79.5, 80, 80.5, 81, 81.5, 82, 82.5, 83, 83.5, 84, 84.5, 85, 85.5, 86, 86.5, 87, 87.5, 88, 88.5, 89, 89.5, 90, 95, 100, 105, 110, 115, 120, 125, 130, 135, 140, 145, 150, 155, 160, 165, 170 mg/kg and FK506 and Rapamycin are provided in doses as listed as Variations 1-20 in Table A. As discussed above, Factor H, FK506, and Rapamycin can be provided in the same composition or in separate compositions to the recipient and may also be administered to the recipient at the same time or at different time points before and/or after transplantation.

TABLE A

Exemplary embodiments of FK506 and Rapamycin concentrations for use in methods of the invention

|  | At least 3 mg/kg Rapamycin | Between 2 and 20 mg/kg Rapamycin | A concentration to reach a plasma level of Rapamycin between 5 and 50 ng/mL | At least 1, 2, 3, 4, 5, 6, 7, 8, 9, 10 mg/kg Rapamycin |
|---|---|---|---|---|
| At least .3 mg/kg FK506 | Var. 1 | Var. 2 | Var. 3 | Var. 4 |

TABLE A-continued

Exemplary embodiments of FK506 and Rapamycin concentrations for use in methods of the invention

| | At least 3 mg/kg Rapamycin | Between 2 and 20 mg/kg Rapamycin | A concentration to reach a plasma level of Rapamycin between 5 and 50 ng/mL | At least 1, 2, 3, 4, 5, 6, 7, 8, 9, 10 mg/kg Rapamycin |
|---|---|---|---|---|
| Between .2 and 2 mg/kg FK506 | Var. 5 | Var. 6 | Var. 7 | Var. 8 |
| Between .3 and 1 mg/kg FK506 | Var. 9 | Var. 10 | Var. 11 | Var. 12 |
| A concentration of FK506 to reach a plasma level of between 0.2 to 1 µg/L of FK506 | Var. 13 | Var. 14 | Var. 15 | Var. 16 |
| At least .1, .2, .3, .4, .5, .6, .7, .8, .9, 1.0 mg/kg FK506 | Var. 17 | Var. 18 | Var. 19 | Var. 20 |

*Var. = Variation

As discussed above, any one of Factor H, FK506, and Rapamycin may be administered systemically or locally. In further embodiments, Factor H, FK506 and Rapamycin may be administered by a method selected independently from intravenous, subcutaneous, intramuscular, and oral means. In further exemplary embodiments in which all three therapies are provided to the recipient, the Factor H can be administered intravenously or intraperitoneally, FK506 can be administered subcutaneously, and Rapamycin can be administered intravenously or intraperitoneally. As will be appreciated, any of these administrations may encompass any of the doses and concentrations discussed herein.

The methods of preventing or inhibiting allograft rejection provided herein further include administering Factor H with or without one or more additional immunosuppressants in a single administration or at repeated intervals after transplantation. In further embodiments, Factor H and/or the one or more immunosuppressants (including without limitation FK506 and/or Rapamycin) are administered to the recipient every 1, 2, 3, 4, 5, 6, 7, 8, 9, 10, 11, 12 months. As will be appreciated, in embodiments in which a combination of therapies is provided to the recipient, the different therapies may be provided to the recipient at different time intervals after transplant of the allograft. For example, in exemplary embodiments, Factor H is provided to the recipient every day and FK506 and Rapamycin are provided to the recipient in any of the dose administrations represented by Variations 21-56 in Table 6. In further exemplary embodiments, Factor H is provided to the recipient every other day and FK506 and Rapamycin are provided to the recipient in any of the dose administrations represented by Variations 21-56 in Table 6. In still further exemplary embodiments, Factor H is provided to the recipient in a concentration and at an interval to maintain a plasma level of factor H of about 1-2 mg/mL, and FK506 and Rapamycin are provided to the recipient in any of the dose administrations represented by Variations 21-56 in Table 6.

TABLE B

Exemplary embodiments of FK506 and Rapamycin dose administrations

| | Rapamycin every day | Rapamycin every other day | Rapamycin once a week | Rapamycin twice a week | Rapamycin once a month | Rapamycin once a month |
|---|---|---|---|---|---|---|
| FK506 every day | Var. 21 | Var. 22 | Var. 23 | Var. 24 | Var. 25 | Var. 26 |
| FK506 every other day | Var. 27 | Var. 28 | Var. 29 | Var. 30 | Var. 31 | Var. 32 |
| FK506 once a week | Var. 33 | Var. 34 | Var. 35 | Var. 36 | Var. 37 | Var. 38 |
| FK506 twice a week | Var. 39 | Var. 40 | Var. 41 | Var. 42 | Var. 43 | Var. 44 |
| FK506 once a month | Var. 45 | Var. 46 | Var. 47 | Var. 48 | Var. 49 | Var. 50 |
| FK506 once a month | Var. 51 | Var. 52 | Var. 53 | Var. 54 | Var. 55 | Var. 56 |

*Var. = Variation every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 days. In further exemplary embodiments, the Factor H and/or the one or more immunosuppressants (including without limitation FK506 and/or Rapamycin) are administered to the recipient every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52 weeks. In further exemplary embodiments, the Factor H and/or the one or more immunosuppressants (including without limitation In still further embodiments and in accordance with any of the above, the administration of Factor H with or without additional administration of one or more immunosuppressants is provided at differing intervals depending on the length of time the recipient has had the allograft. For example, in some exemplary embodiments, Factor H is provided every other day until Post-Operative Day (POD) 14 and then twice a week until at least POD 60. In further embodiments, Factor H is provided every other day until POD 14 and then twice a week until at least POD 60 and FK506 is provided daily until POD10 and then every other day until at least POD60. In still further embodiments, Factor H is provided every other day until POD 14 and then twice a week until at least POD 60 and FK506 is provided daily until POD10 and then every other day until at least POD60 and Rapamycin is provided every day until POD10.

Further exemplary embodiments of treatment regimens are provided in Table C—any one of Factor H or one or more immunosuppressants may be provided in any combination of intervals and lengths of time as represented by Variations 57-84 in Table C.

TABLE C

Exemplary embodiments of treatment regimens

|  | Until at least POD 10 | Until at least POD 14 | Until at least POD 30 | Until at least POD 60 | Until at least POD 120 | Until at least POD 180 |
|---|---|---|---|---|---|---|
| every day until | Var. 57 | Var. 58 | Var. 59 | Var. 60 | Var. 61 | Var. 62 |
| every other day | Var. 63 | Var. 64 | Var. 65 | Var. 66 | Var. 67 | Var. 68 |
| once a week | Var. 69 | Var. 70 | Var. 71 | Var. 72 | Var. 73 | Var. 74 |
| twice a week | Var. 75 | Var. 76 | Var. 77 | Var. 78 | Var. 79 | Var. 80 |
| once a month | N/A | N/A | Var. 81 | Var. 82 | Var. 83 | Var. 84 |

*Var. = Variation

In further embodiments and in accordance with any of the above, Factor H and/or one or more of the immunosuppressants discussed herein may in addition to being administered to the recipient after transplantation of the allograft may also be administered to either the recipient or the allograft or to both the recipient or the allograft before transplantation.

Methods of Treating Rheumatoid Arthritis

In one aspect, the present invention provides methods for treating rheumatoid arthritis in a subject by administering a composition comprising FH to that subject. As discussed above, the FH used to treat the subject may comprise one or more variants of FH, and may be plasma-derived or recombinant.

In specific embodiments, administering FH to a subject in accordance with the methods described herein reduces joint inflammation in the subject. In further embodiments, the amount of FH administered to the subject and/or the length of time FH is administered is an amount effective to reduce joint inflammation in the subject. Methods of assessing and measuring joint inflammation are known in the art and include in non-limiting examples imaging methods and measurement of blood markers of inflammation. Imaging methods include without limitation X-ray, PET scans, micro-CT, MRI, and the like. Blood markers of inflammation include without limitation erythrocyte sedimentation rate, c-reactive protein (CRP), albumin, cholesterol and plasma viscosity.

In further embodiments, administering FH to a subject in accordance with the methods described herein inhibits an initial inflammatory response. In further embodiments, administering FH to a subject in accordance with the methods described herein promotes the resolution of an inflammatory response that is already underway. In still further embodiments, the amount of FH administered to the subject and/or the length of time FH is administered is an amount effective to inhibit an initial inflammatory response and/or promotes the resolution of an inflammatory response in the subject.

In still further embodiments, administering FH to a subject in accordance with the methods described herein results in a reduction of exostosis (an outgrowth of cartilaginous tissue on bone) in the subject. In still further embodiments, the amount of FH administered to the subject and/or the length of time FH is administered is an amount effective to reduce exostosis in the subject.

In further embodiments, administering FH to a subject in accordance with the methods described herein results in a reduction of damage to the cartilage as compared to a subject that has not received FH. In still further embodiments, the amount of FH administered to the subject and/or the length of time FH is administered is an amount effective to reduce damage to cartilage in the subject as compared to a subject that has not received FH.

For any of the methods for preventing or treating rheumatoid arthritis discussed herein, the Factor H discussed may be plasma-derived or recombinant and may further comprise one or more different variants (including full-length and truncated forms). In exemplary embodiments, the Factor H used for treating rheumatoid arthritis includes one or more recombinant protective variants of Factor H that comprise a sequence in accordance with any of the sequences described in U.S. Pat. No. 7,745,389, including SEQ ID NO:5 of U.S. Pat. No. 7,745,389, which is provided herein as SEQ ID NO: 1 in FIG. 12. In further embodiments, a recombinant Factor H is used to treat rheumatoid arthritis in a subject where that recombinant Factor H has at least 70%, 75%, 80%, 85%, 90%, 91%, 92%, 93%, 94%, 95%, 96%, 97%, 98%, 99% and 100% sequence identity to any of the sequences described in U.S. Pat. No. 7,745,389. In still further embodiments, the recombinant Factor H of use in the present invention has at least 70%, 75%, 80%, 85%, 90%, 91%, 92%, 93%, 94%, 95%, 96%, 97%, 98%, 99% and 100% sequence identity to SEQ ID NO:5 of U.S. Pat. No. 7,745,389, which is provided herein as SEQ ID NO: 1 in FIG. 12. In yet further embodiments, the recombinant Factor H used to treat rheumatoid arthritis in accordance with methods of the present invention comprises SEQ ID NO: 1 pictured in FIG. 12 with about 1-100, 3-95, 5-90, 7-85, 9-80, 11-75, 13-70, 15-65, 17-60, 19-55, 21-50, 23-45, 25-40, 27-35 amino acid substitutions. The following discussion of treatment methods utilizing Factor H encompasses plasma derived or recombinant Factor H, including variants thereof, such as one or more of the protective variants discussed herein.

In further embodiments, the amount of FH administered to the subject is an amount effective to reduce inflammation, exostosis, or damage to cartilage as described above. In still further embodiments and as discussed above for prevention or inhibition of allograft rejection, the amount of FH administered to a subject with rheumatoid arthritis may vary, but in general is in a range effective to inhibit complement activation. Complement inhibition can be evaluated based on any methods known in the art, including for example, in vitro zymosan assays, assays for lysis of erythrocytes, immune complex activation assays, and mannan activation assays. In some embodiments, the CR2-FH has one or more of the following properties of FH: (1) binding to C-reactive protein (CRP), (2) binding to C3b, (3) binding to heparin, (4) binding to sialic acid, (5) binding to endothelial cell surfaces, (6) binding to cellular integrin receptor, (7) binding to pathogens, (8) C3b co-factor activity, (9) C3b decay-acceleration activity, and (10) inhibiting the alternative complement pathway.

In further exemplary embodiments, the amount of FH used is in an amount effective to achieve a plasma concentration of about 1-2 mg/ml. In further embodiments, the amount of FH used for treatment is about 86 mg/kg. The FH may be administered to the subject one or more times at a range of intervals for a period of days, weeks or months, as is described in further detail herein.

In some aspects of the invention, Factor H can be administered to the recipient by intravenous, intraocular, subcutaneous, and/or intramuscular means. In further aspects, the Factor H and/or immunosuppressant compositions herein can be administered either systemically or locally to treat rheumatoid arthritis. Systemic administration includes without limitation oral, transdermal, subdermal, intraperitoneal, intravenous, subcutaneous, transnasal, sublingual, or rectal. Local administration may include without limitation administration directly to one or more joints via perfusion, injection (including intra-articular injection) or other contact with the one or more joints, or via a sustained delivery device implanted at or near one or more joints affected by the rheumatoid arthritis. Local administration to joints may include administration to any joints particularly affected by rheumatoid arthritis, including without limitation joints of the hands, feet, cervical spine, shoulder and knee.

In accordance with any of the above, the FH provided to the recipient to treat rheumatoid arthritis is in a therapeutically effective dose between about 0.05 mg/mL and about 10 mg/mL. In other embodiments, Factor H is administered at a concentration of between about 0.1 mg/mL and about 10 mg/mL. In yet other embodiments, Factor H is administered at a concentration of between about 0.1 mg/mL and about 5 mg/mL. In another embodiment, Factor H is administered at a concentration of between about 0.1 mg/mL and about 2 mg/mL. In another embodiment, Factor H is administered at a concentration of between about 1 mg/mL and about 2 mg/mL. In yet other embodiments, Factor H is administered at about 0.01 mg/mL, or at about 0.02 mg/mL, 0.03 mg/mL, 0.04 mg/mL, 0.05 mg/mL, 0.06 mg/mL, 0.07 mg/mL, 0.08 mg/mL, 0.09 mg/mL, 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, 1.0 mg/mL, 1.1 mg/mL, 1.2 mg/mL, 1.3 mg/mL, 1.4 mg/mL, 1.5 mg/mL, 1.6 mg/mL, 1.7 mg/mL, 1.8 mg/mL, 1.9 mg/mL, 2.0 mg/mL, 2.5 mg/mL, 3.0 mg/mL, 3.5 mg/mL, 4.0 mg/mL, 4.5 mg/mL, 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10.0 mg/mL, or a higher concentration. In further embodiments, Factor H is administered at a concentration in a range of about 0.1-15, 0.3-14.5, 0.5-14, 0.7-13.5, 0.9-13, 1.1-12.5, 1.3-12, 1.5-11.5, 1.7-11, 1.9-10.5, 2.1-10, 2.3-9.5, 2.5-9, 2.7-8.5, 2.9-8, 3.1-7.5, 3.3-7, 3.5-6.5, 3.7-6, 3.9-5.5, 4.1-5, 4.3-4.5 mg/mL.

In still further embodiments, aqueous Factor H compositions comprising a protein concentration of at or about between 10 g/L and 250 g/L are administered to a subject for treatment of rheumatoid arthritis. In certain embodiments, the protein concentration of the Factor H composition is at or about between 50 g/L and 200 g/L, or at or about between 70 g/L and 150 g/L, or at or about between 90 g/L and 120 g/L, or at or about between 30 g/L and 70 g/L, or at or about between 40 g/L and 60 g/L or any suitable concentration within these ranges, for example at or about 10 g/L, or at or about 15 g/L, 20 g/L, 25 g/L, 30 g/L, 35 g/L, 40 g/L, 45 g/L, 50 g/L, 55 g/L, 60 g/L, 65 g/L, 70 g/L, 75 g/L, 80 g/L, 85 g/L, 90 g/L, 95 g/L, 100 g/L, 105 g/L, 110 g/L, 115 g/L, 120 g/L, 125 g/L, 130 g/L, 135 g/L, 140 g/L, 145 g/L, 150 g/L, 155 g/L, 160 g/L, 165 g/L, 170 g/L, 175 g/L, 180 g/L, 185 g/L, 190 g/L, 195 g/L, 200 g/L, 205 g/L, 210 g/L, 215 g/L, 220 g/L, 225 g/L, 230 g/L, 235 g/L, 240 g/L, 245 g/L, 250 g/L, or higher. In a preferred embodiment, Factor H compositions having high protein concentrations will also high levels of purity. In one embodiment, at least 90% of the protein in the composition will be Factor H. In a preferred embodiment, at least 95% of the protein in the composition will be Factor H.

In further embodiments, Factor H is provided for treatment of rheumatoid arthritis in a therapeutically effective dose that results in a plasma level concentration in the recipient of about 0.05 mg/mL and about 10 mg/mL. In other embodiments, Factor H is provided in a therapeutically effective dose that results in a plasma level concentration in the recipient of between about 0.1 mg/mL and about 10 mg/mL. In yet other embodiments, Factor H is provided in a therapeutically effective dose that results in a plasma level concentration in the recipient of between about 0.1 mg/mL and about 5 mg/mL. In another embodiment, Factor H is provided in a therapeutically effective dose that results in a plasma level concentration in the recipient of between about 0.1 mg/mL and about 2 mg/mL. In another embodiment, Factor H is provided in a therapeutically effective dose that results in a plasma level concentration in the recipient of between about 1 mg/mL and about 2 mg/mL. In yet other embodiments, Factor H results in a plasma concentration of at about 0.01 mg/mL, or at about 0.02 mg/mL, 0.03 mg/mL, 0.04 mg/mL, 0.05 mg/mL, 0.06 mg/mL, 0.07 mg/mL, 0.08 mg/mL, 0.09 mg/mL, 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, 1.0 mg/mL, 1.1 mg/mL, 1.2 mg/mL, 1.3 mg/mL, 1.4 mg/mL, 1.5 mg/mL, 1.6 mg/mL, 1.7 mg/mL, 1.8 mg/mL, 1.9 mg/mL, 2.0 mg/mL, 2.5 mg/mL, 3.0 mg/mL, 3.5 mg/mL, 4.0 mg/mL, 4.5 mg/mL, 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10.0 mg/mL, or a higher concentration. In further embodiments, Factor H is provided in a therapeutically effective dose that results in a plasma level concentration in the recipient in a range of about 0.1-15, 0.3-14.5, 0.5-14, 0.7-13.5, 0.9-13, 1.1-12.5, 1.3-12, 1.5-11.5, 1.7-11, 1.9-10.5, 2.1-10, 2.3-9.5, 2.5-9, 2.7-8.5, 2.9-8, 3.1-7.5, 3.3-7, 3.5-6.5, 3.7-6, 3.9-5.5, 4.1-5, 4.3-4.5 mg/mL. The plasma level concentration may be determined using standard assays known in the art.

In further embodiments, Factor H is provided in a therapeutically effective dose of about 50-150 mg/kg for treatment of rheumatoid arthritis. In still further embodiments, Factor H is provided in a therapeutically effective dose of about 52-145, 54-140, 56-135, 58-130, 60-125, 62-120, 64-115, 66-110, 68-105, 70-100, 72-95, 74-90, 76-87, 78-86, 80-85 mg/kg. In still further embodiments, Factor H is provided in a therapeutically effective dose of about 70, 70.5, 71, 71.5, 72, 72.5, 73, 73.5, 74, 74.5, 75, 75.5, 76, 76.5, 77, 77.5, 78, 78.5, 79, 79.5, 80, 80.5, 81, 81.5, 82, 82.5, 83, 83.5, 84, 84.5, 85, 85.5, 86, 86.5, 87, 87.5, 88, 88.5, 89, 89.5, 90, 95, 100, 105, 110, 115, 120, 125, 130, 135, 140, 145, 150, 155, 160, 165, 170 mg/kg.

The methods of treating rheumatoid arthritis provided herein further include administering Factor H in a single administration or at repeated intervals. In further embodiments, Factor H is administered to the recipient every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 days. In further exemplary embodiments, the Factor H is administered to the recipient once every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52 weeks. In further exemplary embodiments, Factor H is administered to the recipient every 1, 2, 3, 4, 5, 6, 7, 8, 9, 10, 11, 12 months.

In still further embodiments and in accordance with any of the above, Factor H is provided at differing intervals. For example, and as is discussed above, Factor H can be administered for a sufficient length of time to reduce joint inflammation. In some exemplary embodiments, Factor H can be administered every other day until inflammation is reduced. In further exemplary embodiments, Factor H can be provided in an initial bolus to result in a plasma level above 1-5 mg/ml and then additional administrations of Factor H can be provided every 1 2, 3, 4, 5, 6, 7, 8, 9, 10, 11, 12, 13, or 14 days until inflammation is reduced.

EXAMPLES

Example 1

Use of Factor H for Treating Transplant Rejection

Male C3H (H-2k) and C57BL/6 (B6, H-2b) mice (25-30 g) were used to determine the efficacy of Complement Factor H (CFH) during transplant rejection. C3H mice served as skin graft and kidney donors for pre-sensitization and kidney transplantation. Male C57BL/c (B6) mice were used as recipients. The B6 recipients were pre-sensitized by transplantation of the donor skin grafts, and were subsequently transplanted with kidney allografts between 15 and 20 days after the skin transplantation. B6 mice were treated with vehicle (controls), CFH (day −1, day 0, then every other day to day 10; 8 mg/mouse, i.p.), FK506 (daily from day −1 to day 10; 1 mg/kg s.c.) or the combination of CFH+FK506 using the same dosage regime as the single treatments. Mice were monitored daily for signs of rejection. Renal function was monitored by measuring serum creatinine levels.

Figure 2:
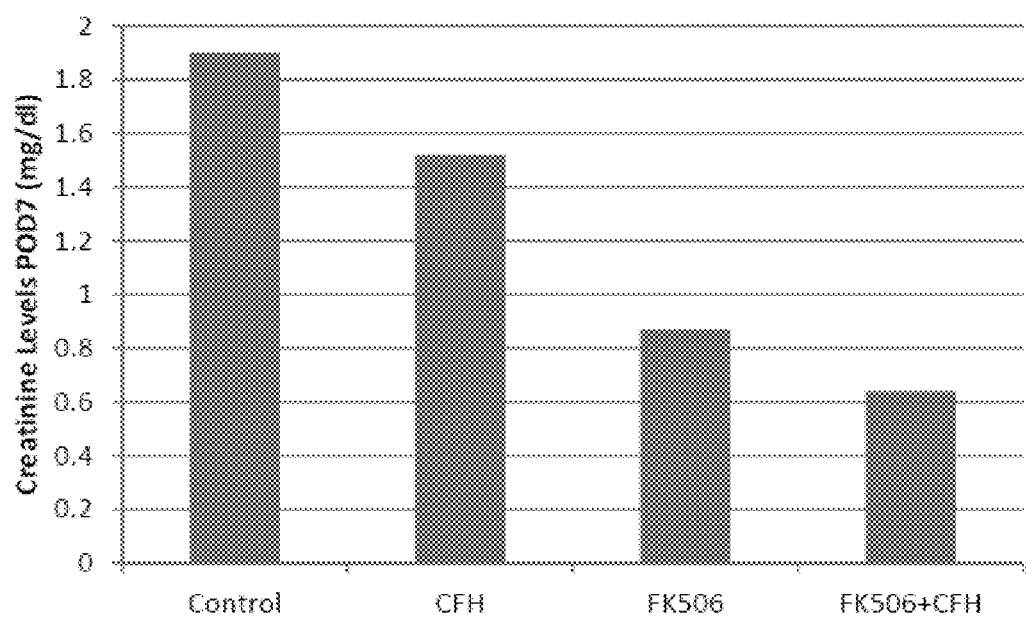
FIG. 2 illustrates creatinine levels on POD7 in pre-sensitized mouse allograft model treated with CFH, FK506, or CFH+FK506.

Untreated C3H kidneys grafted into pre-sensitized recipients were rejected rapidly, as indicated by an increased creatinine (Cr) level measured on POD7 (FIG. 2). Untreated grafts lost graft function (Cr>2 mg/dl) with a median survival of 7.5 days due to graft function deterioration. Treatment with CFH alone reduced plasma Cr levels (1.4±0.2 mg/dl, vs. 1.9±0.1 in controls), thus improving renal allograft function. CFH in combination with FK506 further improved graft function, suggesting that CFH can limit IRI in the acute transplant setting (FIG. 2).

Example 2

Use of Rapamycin in Combination with Factor H for Treating Transplant Rejection Male C3H (H-2k) and C57BL/6 (B6, H-2b) mice (25-30 g) were used to determine the efficacy of Rapamycin (RAPA) in combination with Factor H (FH) during transplant rejection. C3H mice served as skin graft and kidney donors for pre-sensitization and kidney transplantation. Male C57BL/c (B6) mice were used as recipients. The B6 recipients were pre-sensitized by transplantation of the donor skin grafts, and were subsequently transplanted with kidney allografts between 15 and 20 days after the skin transplantation. Transplanted B6 mice were treated with Rapamycin (RAPA) alone (daily from day-1 to day 10; 0.3 mg/kg, i.p.), RAPA+CFH (CFH treatment=day −1, day 0, then every other day to day 14, then 2× per week to endpoint; 8 mg/mouse, i.p., CFH i.p. recipients also received an IV infusion of a single dose infusion of Adrenomedullin mixed with CFH during transplant surgery, 100 µg/kg; RAPA treatment=daily from day-1 to day 10; 0.3 mg/kg, i.p.), RAPA+FK506 (FK=daily from day −1 to day 10, then every other day to endpoint; 3 mg/kg s.c.; RAPA=daily from day-1 to day 10; 0.3 mg/kg, i.p.) or the combination of RAPA+CFH+FK506 using the same dosage regime as above. The experimental groups were a) C3H to B6 txs+pre-sensitization+RAPA; b) C3H to B6 txs+pre-sensitization+CFH+RAPA; c) C3H to B6 txs+pre-sensitization FK+RAPA; and d) C3H to B6 txs+pre-sensitization+CFH+FK+RAPA. ("txs"="transplantation/skin graft")

Mice were monitored daily for signs of rejection and were euthanized at the end point of the experiment, which was defined as when transplants developed functional deterioration due to severe rejection or on POD60 and POD100. Renal graft function was monitored by plasma creatinine (Cr) blood urea nitrogen (BUN) and hematocrit (Hct) levels by an I-Stat potable analyzer (Abaxis). Circulating donor specific antibodies (DSAs) were determined prior to kidney transplantation and at the endpoint of study by flow cytometry.

Figure 3:
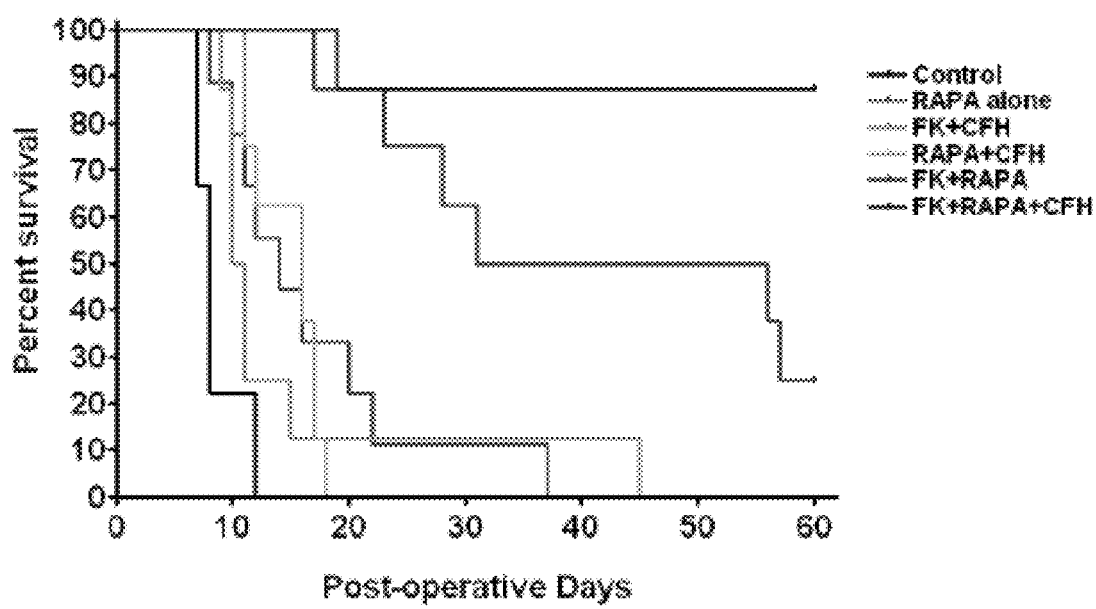
FIG. 3 illustrates a Kaplan Meier Survival Curve of kidney transplants in the pre-sensitized recipients. P<0.05, FK+RAPA vs. CFH+FK+RAPA. FK+CFH cohort, stopped all treatment at day 10.

CFH in combination with RAPA and FK (CFH+RAPA+FK) protected kidney allograft rejection from acute AMR and CMR, and prolonged kidney allograft survival in the pre-sensitized recipients. As shown in Table 1 and FIG. 3, short-term RAPA monotherapy or RAPA in combination with CFH (CFH+RAPA) demonstrated a protective effect. With an improvement of early graft function at POD7 (FIG. 4), treatment with RAPA alone or RAPA+FH prolonged the allograft survival from 8 days (mean survival time—"MST") in the untreated allografts (controls) to 14 and 16 days (MST), respectively. Treatment with RAPA and FK combination (RAPA+FK) further prolonged the renal allograft survival to 44 days (MST). Triple therapy with CFH+RAPA+FK effectively prevented graft rejection and achieved long-term kidney allograft survival. As a result, 87.5% (⅞) of the renal allografts with the triple therapy achieved long-term survival (>60 days) (p<0.05 vs. RAPA+FK).

TABLE 1

Individual graft survival in pre-sensitized kidney transplant model.

| Cohort | Survival (days) | MST |
|---|---|---|
| RAPA Alone | 8, 8, 10, 11, 12, 22, 14, 16, 20, 37 | 14 |
| RAPA + CFH | 11, 11, 12, 16, 16, 17, 17, 18 | 16 |
| RAPA + FK506 | 7, 17, 23, 28, 31, 56[1], 57[1], >60[3], >60[3,4] | 44 |
| RAPA + FK506 + CFH | 19, >60[2], >60[2], >60[2], >60[2], >60[3], >60[3], >60[3] | >60 |

Treatment with CFH+RAPA+FK preserved long-term renal allograft function in the pre-sensitized recipients. To evaluate the influence of CFH on renal function, plasma samples were collected from the kidney allografts. Cr, BUN (Blood Urea Nitrogen) and Hematocrit (Hct) were measured on POD7, POD21, and POD60, or terminal rejection. The plasma concentrations of the waste substances, such as Cr and BUN, are commonly used in clinical practice to determine renal function. Elevation of Cr and BUN beyond the normal range (in normal B6 mice, Cr=0.2±0.05 mg/dl, BUN=34±8.81 mg/dl) indicates a loss of kidney function. The hematocrit is the volume percentage (%) of red blood cells in blood. A decrease in Hct (normal Hct-44±1.73% PCV) is associated with kidney injuries due to decreased production of the hormone erythropoietin.

Figure 4:
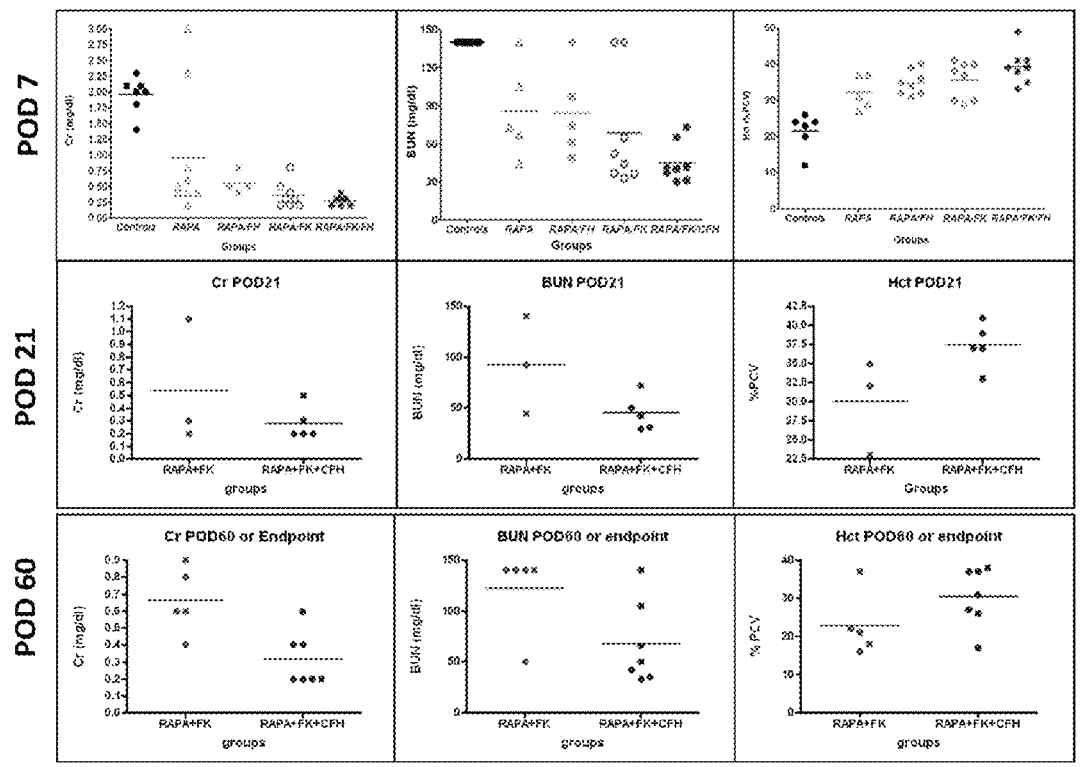
FIG. 4 illustrates renal function in the different cohorts over time. In normal B6 mice, Cr=0.2±0.05 (mg/dl), BUN=34±8.81 (mg/dl), Hct-44±1.73 (% PCV).

The results in FIG. 4 show that the Cr and BUN levels were increased in the controls on POD7. While all immunotherapies with RAPA or RAPA+CFH or RAPA+FK demonstrated protection of early renal function (POD7) with reduced Cr and BUN and increased Hct compared to controls, the triple therapy achieved long-term improvement of renal function as indicated by decreased Cr and BUN levels, and increased Hct (FIG. 4) on POD21 and at the endpoint (rejection or POD60) as compared to the treatment with only FK and RAPA.

To determine whether continued treatment with FK and CFH could further extend graft survival, the remaining two kidney allografts with RAPA+FK and three with CFH+RAPA+FK were followed up until POD100. As shown in Table 2, the results indicated that all transplants with the triple therapy survived to 100 days and maintained normal renal function.

TABLE 2

Long term survival of grafts in pre-sensitized kidney transplant model.

| Cohorts | Mouse ID | Weight Change | sCr (mg/dl) | uCr (mg/dl) | BUN | Hct |
|---|---|---|---|---|---|---|
| RAPA + FK | PST154 | Increased | 0.3 | >20[1] | 34 | 36 |
| RAPA + FK | PST157 | Decreased | 0.7 | 5.6 | >140 | 18 |
| RAPA + FK + CFH | PST151 | Increased | 0.2 | 16.7 | 60 | 30 |
| RAPA + FK + CFH | PST155 | Increased | 0.2 | >20[1] | 31 | 39 |
| RAPA + FK + CFH | PST156 | Increased | 0.2[1] | 17.4 | 43 | 29 |

Figure 5:
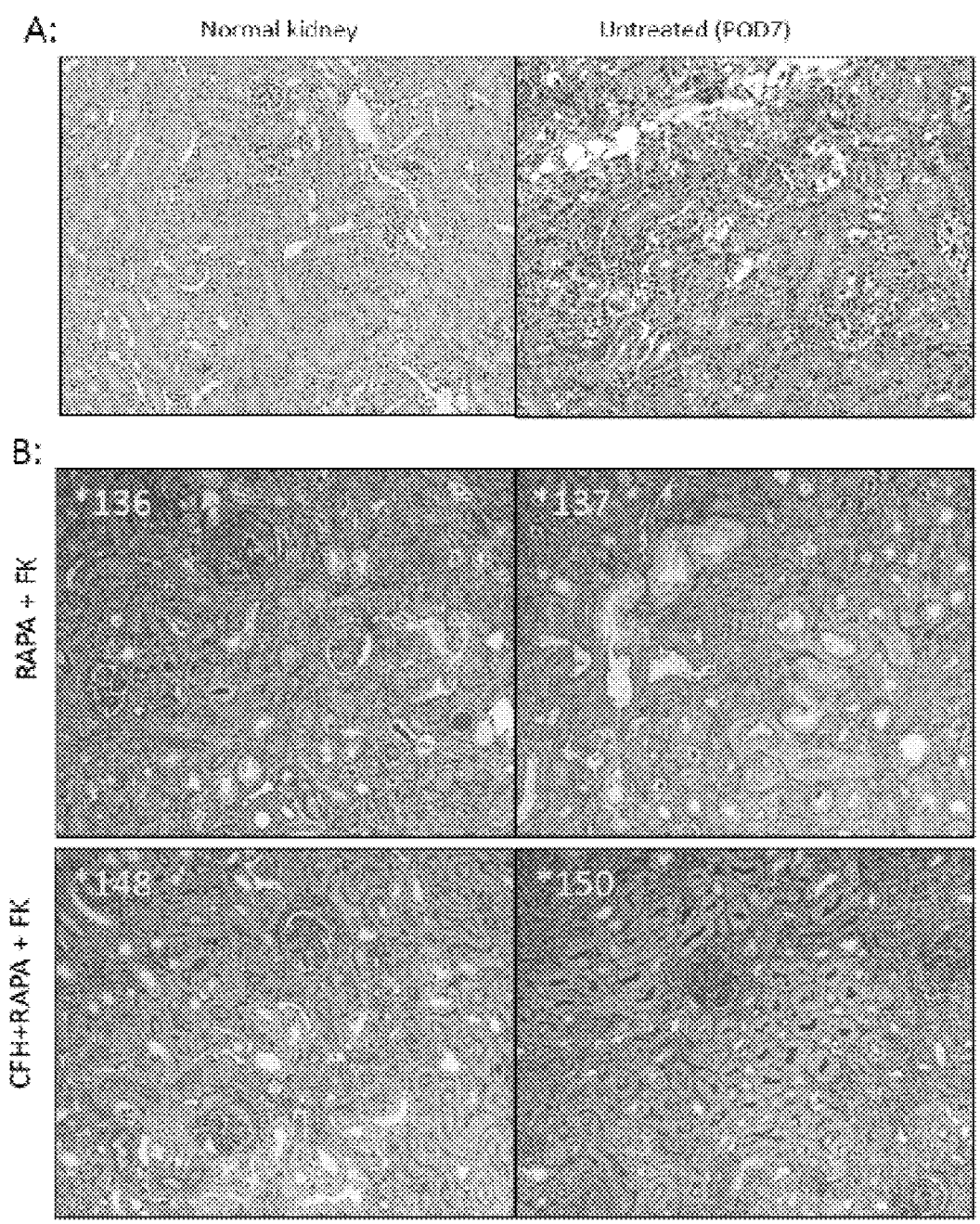
FIG. 5 illustrates representative histological images of kidney allografts. A) A normal kidney is shown on the left; an untreated transplant (POD7) is shown on the right. B) The top frames are allografts from RAPA+FK506 treated mice (#136, #137); the bottom frames are allografts from RAPA+FK506+ CFH treated mice (#148, #150).

Histological examination revealed heterogeneous changes. The grafts that were rejected within 4 weeks showed severe AMR and CMR (data not shown), with a histological rejection features similar to those observed in untreated pre-sensitized recipients (FIG. 5A), regardless of whether they were treated with RAPA alone, RAPA+CFH, or RAPA+FK. In contrast, transplants with CFH+RAPA+FK triple therapy showed less inflammation and tubular damage with decreased monocyte infiltration, decrease tubular atrophy and segmental glomerulosclerosis, and decreased fibrotic changes in comparison with FK/RAPA treated grafts when examined at 8 weeks (FIG. 5B). Furthermore, the CFH+RAPA+FK triple therapy reduced the severity of AMR injuries (peritubular capillaritis, glomerularitis, and glomerular thrombi and mesangiolysis).

Example 3

The Effect of CFH in Combination with Adrenomedullin for Treating Transplant Rejection The effect of CFH with or without Adrenomedullin (AM) on kidney graft function, antibody response, and histology was determined following the early phase of transplantation (POD3 and POD5). The pre-sensitized kidney transplants were treated with CFH (8 mg, i.p.) on day −1, day 0 and then every other day. To test whether AM provides additional benefits to renal graft function, an additional group of transplants were treated with a single dose infusion (200 µl, i.v.) of AM (~100 ug/kg) mixed with CFH (~1 mg/kg) immediately following the transplant surgery (POD0), in addition to the i.p. injection of CFH (day-1, 0, and every other day).

CFH is a serum-binding protein for AM. It has been shown that AM influences the complement regulatory function of Factor H by enhancing the cleavage of C3b via Factor I. Preparation of AM+CFH solution was prepared as follows: a) dissolve vial contents of AM (100 µg) in 4.166 ml of sterile saline (to make a 24 µg/ml working stock solution); b) dilute 14.4 µl of 15.6 mg/ml FH stock in 985.6 µl of sterile saline (to make a 225 µg/ml working stock solution of FH); c) mix equal volumes (950 µl each) of the 24 µg/ml working stock of AM with the 225 µg/ml working stock of FH to make the final infusion solution (AM concentration will be 12 µg/ml; FH concentration will be 112.5 µg/ml). Transfer 220 µl aliquots to sterile tubes and freeze at −70 until ready for use.

All mice were sacrificed on POD3 and 5, respectively (~5/ea). Untreated transplants sacrificed at the same endpoints were used as controls. Graft tissues were harvested for histology and immune-histochemistry (IHC). The experimental groups were as follows: 1) C3H to B6 txs+pre-sensitization+control; 2) C3H to B6 txs+pre-sensitization+CFH (i.p.); and 3) C3H to B6 txs+pre-sensitization+CFH (i.p.)+AM/CFH infusion (at time of transplant).

Figure 6:
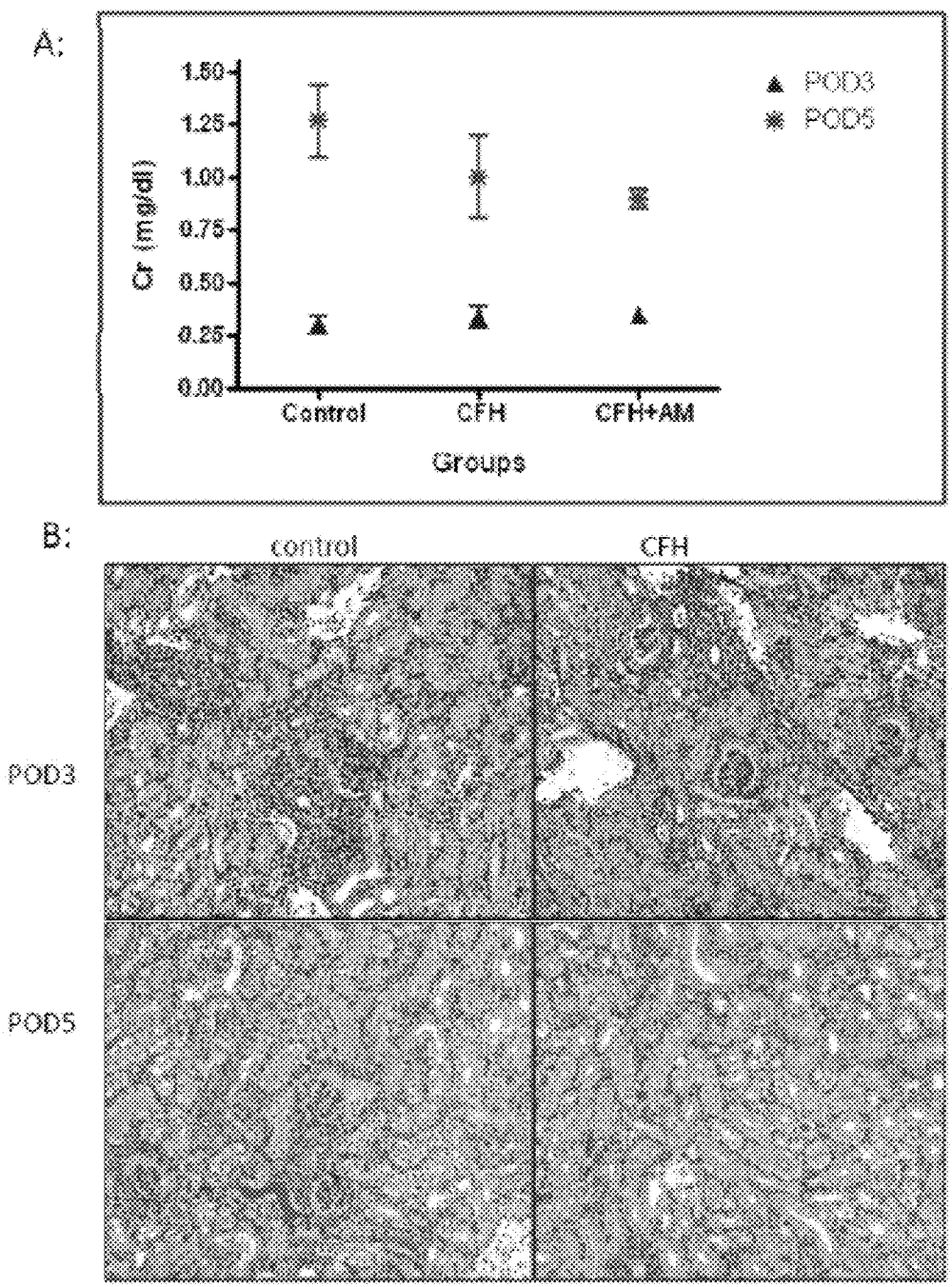
FIG. 6 illustrates A) renal function analysis (n=4 to 6 per group); and B) representative histological images of kidney allografts on POD3 and POD5.

As shown in FIG. 6A, Cr levels increased by POD5 in untreated transplants (P<0.01, vs. normal B6). CFH alone and CFH with AM+CFH as a single infusion treatment showed a trend of improved renal function as the mean Cr level in these groups were lower compared to the controls. Addition of a single dose AM/CFH infusion was beneficial in further reducing the Cr level on POD5.

Histological examinations by hematoxylin and eosin (HE) staining (FIG. 6B) revealed that control kidney allografts in the pre-sensitized recipients had early signs of mixed acute cellular and humoral rejection by POD5 (mononuclear cell infiltration, endothelium activation, edema, focal acute renal tubular necrosis). The kidney grafts treated with CFH showed an improved morphology with less tubular necrosis on POD5.

Figure 7:
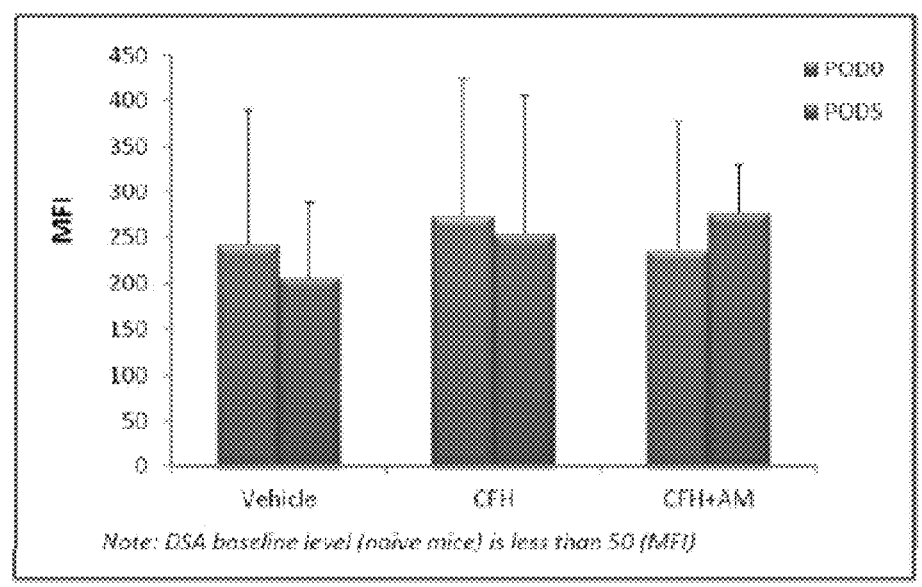
FIG. 7 illustrates A) pre- and post-transplant plasma DSA (IgG) levels; and B) lack of correlation between IgG levels and Cr levels.
Figure 7:
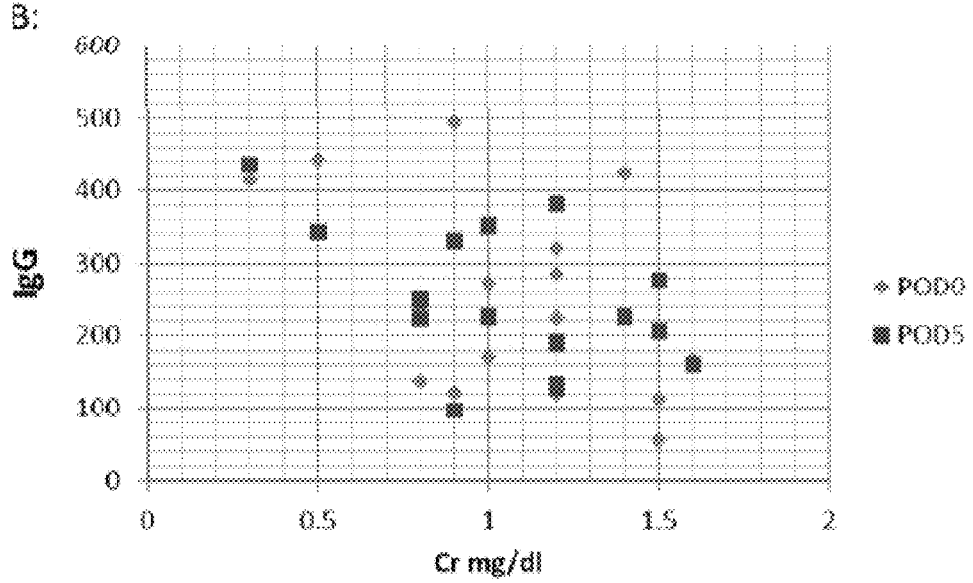

To determine plasma DSA levels, plasma samples from kidney transplant recipients were collected one day prior to kidney transplantation (2 weeks after donor skin graft pre-sensitization) and the endpoint of the study. DSA levels were measured by flow cytometry. FIG. 7 shows that a significant increase of DSA (IgG) and IgG levels as expressed by mean channel fluorescence intensity (MFI) were comparable among the groups. There was no correlation between IgG levels and Cr levels (FIG. 7B).

Example 4

Use of Factor H for Treating Rheumatoid Arthritis

Balb C mice (n=10 per cohort) were used to determine the efficacy of Factor H (FH) during transplant rejection. The mice were treated with ArthritoMAb (anti-collagen) antibody cocktail (2 mg, i.v.) on day 1, followed 7 days later with an injection of LPS (50 µg, i.p.). On day 8, hind paw volumes were measured for each animal and distributed to various treatment groups.

Factor H was formulated in 20 mM Citrate, 150 mM NaCl, pH=6. Dexamethasone was formulated in 0.5% hydroxypropylmethyl cellulose/0.2% Tween 80. Ethanercept was formulated as Enbrel™ in saline. Vehicle was formulated in 20 mM Citrate, 150 mM NaCl, pH=6. The dosing volume for dexamethasone and etanercept was 10 mL/kg (0.200 mL/20 g mouse) and adjusted accordingly for body weight. The dosing volume for Factor H and BX12 was 25 mL/kg (0.500 mL/20 g mouse) and adjusted accordingly for body weight.

Dosing with the different agents was started on day 8 as described in Table 3.

TABLE 3

Drug and treatment schedule.

| Agent | Dose (mg/kg) | Route | Schedule |
|---|---|---|---|
| Vehicle | — | i.p. | qodx7 |
| Dexamethasone | 3.32 | oral | qdx14 |
| Etanercept | 10 | i.p. | days 8, 10, 12, 15, 17, 19 |
| Factor H | 440 | i.p. | qodx7 |

Hind paw volumes were measured on day 8, 11, 12, 13, 15, 19 and 22 (endpoint). The age at start date was 7 to 9 weeks. Body weights were measured bi-weekly to the endpoint (Table 4). At the endpoint, tissue samples were processed for histology and submitted to a pathologist for independent analysis. Sampling 1 was performed at the endpoint. The hind limbs were preserved in 10% formalin. Sampling 2 was performed at the endpoint for group 4 animals. Blood was collected by terminal cardiac puncture. The blood was processed for anti-coagulant. The kidneys were additionally preserved in formalin and followed with 70% EtOH. Samples were scored for inflammation, pannus (granulation tissue), cartilage damage, bone resorption and exostosis (Table 5).

TABLE 4

Body weight measurements.

| | Body Weight | | | | | | |
|---|---|---|---|---|---|---|---|
| | Date | | | | | | |
| | Jun. 17, 2011 | Jun. 21, 2011 | Jun. 24, 2011 | Jun. 28, 2011 | Jul. 1, 2011 | Jul. 5, 2011 | Jul. 8, 2011 |
| | Day of Study | | | | | | |
| A# | 1 Wt (g) | 5 Wt (g) | 8 Wt (g) | 12 Wt (g) | 15 Wt (g) | 19 Wt (g) | 22 Wt (g) |
| Group 1: vehicle (ip, qod x 7) | | | | | | | |
| 1 | 18.1 | 18.6 | 16.8 | 18.1 | 18.1 | 17.5 | 17.1 |
| 2 | 17.8 | 18.5 | 16.4 | 17.7 | 17.9 | 18 | 18.5 |
| 3 | 17.3 | 17.9 | 15.7 | 16.3 | 16.5 | 17.5 | 17.3 |
| 4 | 17.9 | 17.1 | 16.4 | 17.9 | 17.7 | 18.1 | 18.8 |
| 5 | 16.8 | 17.8 | 16.5 | 17 | 17.3 | 18.2 | 18.6 |
| 6 | 16.5 | 18.4 | 15.4 | 15.6 | 16 | 17.4 | 17.6 |
| 7 | 16.9 | 17 | 15.5 | 16.7 | 16.9 | 17.5 | 17.7 |
| 8 | 17 | 18.5 | 15.2 | 15.2 | 15.9 | 16.4 | 17.4 |
| 9 | 18 | 17.6 | 16 | 17.4 | 17.9 | 19.1 | 18.9 |
| 10 | 16.8 | 17.3 | 15.4 | 15.6 | 16.5 | 17.7 | 17.7 |
| Mean | 17.3 | 17.9 | 15.9 | 16.8 | 17.1 | 17.7 | 18 |
| STDEV | 0.6 | 0.6 | 0.6 | 1 | 0.8 | 0.7 | 0.7 |
| n | 10 | 10 | 10 | 10 | 10 | 10 | 10 |
| Group 2: dexamethasone (3.32 mg/kg, po, qd x 14 (start on day 8)) | | | | | | | |
| 1 | 16.5 | 18.4 | 17.1 | 16.9 | 16.9 | 16.7 | 17.1 |
| 2 | 16.7 | 16.3 | 16.9 | 17.5 | 17.6 | 16.4 | 17 |
| 3 | 17.7 | 17.3 | 16.1 | 16.9 | 16.9 | 16.9 | 16.9 |
| 4 | 18.1 | 16.9 | 15.6 | 16.3 | 16.2 | 16.4 | 16.5 |
| 5 | 16.2 | 18.6 | 16.6 | 16.8 | 16.8 | 16.7 | 16.5 |
| 6 | 18.2 | 18.5 | 15.6 | 16.9 | 16.7 | 16.7 | 16.2 |
| 7 | 18.7 | 17.3 | 17.1 | 17.9 | 18.2 | 17.5 | 17.6 |
| 8 | 17.2 | 18 | 15.8 | 15.9 | 15.1 | 15.7 | 15.4 |
| 9 | 18.4 | 18.6 | 16.3 | 16.7 | 16.5 | 15.9 | 16 |
| 10 | 18.9 | 18.6 | 15.9 | 16.5 | 15.8 | 16 | 16.1 |
| Mean | 17.7 | 17.9 | 16.3 | 16.8 | 16.7 | 16.5 | 16.5 |
| STDEV | 1 | 0.8 | 0.6 | 0.6 | 0.9 | 0.5 | 0.6 |
| n | 10 | 10 | 10 | 10 | 10 | 10 | 10 |
| Group 3: etanercept (10 mg/kg, ip, days 8, 10, 12, 15, 17, 19) | | | | | | | |
| 1 | 16.7 | 18.5 | 16.5 | 16.6 | 17.1 | 18.3 | 18.8 |
| 2 | 17.3 | 17.4 | 16.4 | 16.7 | 17.8 | 18.3 | 18.3 |
| 3 | 16.5 | 18.2 | 16.1 | 16.7 | 17 | 17.7 | 17.8 |
| 4 | 18 | 16.6 | 16.4 | 17.8 | 17.7 | 18.4 | 18.7 |
| 5 | 16.5 | 17.4 | 15.7 | 15.9 | 16.6 | 14.6 | 15.8 |
| 6 | 17.7 | 18.5 | 16.1 | 17.8 | 18 | 18.8 | 18 |
| 7 | 17.5 | 17.3 | 16.2 | 17.9 | 17.9 | 18.6 | 18.2 |
| 8 | 16.8 | 17 | 15.7 | 15.5 | 16.2 | 16.5 | 17.3 |
| 9 | 17.6 | 18.1 | 16.6 | 17.1 | 17.6 | 18.6 | 18.6 |
| 10 | 18 | 18.3 | 17.1 | 17.7 | 18 | 19.1 | 19.6 |
| Mean | 17.3 | 17.7 | 16.3 | 17 | 17.4 | 17.9 | 18.1 |
| STDEV | 0.6 | 0.7 | 0.4 | 0.8 | 0.6 | 1.4 | 1 |
| n | 10 | 10 | 10 | 10 | 10 | 10 | 10 |
| Group 4: BX12 (440 mg/kg, ip, qod x 7 (start on day 8)) | | | | | | | |
| 1 | 17.1 | 17.6 | 16.8 | 17.9 | 18.1 | 18.5 | 18.6 |
| 2 | 17.9 | 17.8 | 15.5 | 15.4 | 16.8 | 17.4 | 17.1 |
| 3 | 17.1 | 18.2 | 16.2 | 16.1 | 17.8 | 17.2 | 18 |
| 4 | 17.2 | 17.5 | 15.6 | 17.1 | 17.4 | 17.2 | 16.9 |
| 5 | 17.5 | 17.4 | 16.4 | 17.9 | 16.9 | 17.9 | 18.2 |
| 6 | 17 | 18.1 | 15.5 | 16.2 | 17.2 | 17.9 | 17.7 |
| 7 | 17.4 | 17.6 | 15.5 | 18 | 17.8 | 18.4 | 18.4 |
| 8 | 17.4 | 18.3 | 16.5 | 17.9 | 18.1 | 18.5 | 18.8 |
| 9 | 18.1 | 17.6 | 17.4 | 18.3 | 18.6 | 18.8 | 18.3 |
| 10 | 17.1 | 18.2 | 15.5 | 15.7 | 16.7 | 16.7 | 17.1 |
| Mean | 17.4 | 17.8 | 16.1 | 17.1 | 17.5 | 17.9 | 17.9 |
| STDEV | 0.4 | 0.3 | 0.7 | 1.1 | 0.6 | 0.7 | 0.7 |
| n | 10 | 10 | 10 | 10 | 10 | 10 | 10 |

TABLE 5

Histology scores

| Tissue | Group | Animal | Inflammation | Pannus | Cartilage Damage | Bone Resorption | Periosteal/ Exostotic Changes | Composite Biohisto- pathology Score |
|---|---|---|---|---|---|---|---|---|
| Ankle | Group 1 | | 2.0 ± 0.5 | 1.0 ± 0.3 | 0.5 ± 0.2 | 0.6 ± 0.3 | 2.6 ± 0.7 | 6.7 ± 1.7 |
| Ankle | Group 2 | | 0.1 ± 0.1 | 0.1 ± 0.1 | 0.0 ± 0.0 | 0.0 ± 0.0 | 0.0 ± 0.0 | 0.2 ± 0.1 |
| Ankle | Group 3 | | 1.5 ± 0.5 | 1.4 ± 0.5 | 0.7 ± 0.3 | 1.0 ± 0.4 | 1.4 ± 0.6 | 6.0 ± 2.1 |
| Ankle | Group 4 | | 1.0 ± 0.3 | 0.9 ± 0.3 | 0.6 ± 0.2 | 0.3 ± 0.2 | 0.3 ± 0.3 | 3.1 ± 1.2 |
| Ankle | Group 1 | An 1 | 3 | 1 | 0 | 0 | 4 | 0 |
| Ankle | Group 1 | An 2 | 3 | 2 | 1 | 1 | 5 | 13 |
| Ankle | Group 1 | An 3 | 0 | 0 | 0 | 0 | 0 | 0 |
| Ankle | Group 1 | An 4 | 0 | 0 | 0 | 0 | 0 | 0 |
| Ankle | Group 1 | An 5 | 0 | 0 | 0 | 0 | 0 | 0 |
| Ankle | Group 1 | An 6 | 3 | 2 | 1 | 1 | 4 | 11 |
| Ankle | Group 1 | An 7 | 3 | 1 | 0 | 0 | 4 | 0 |
| Ankle | Group 1 | An 8 | 4 | 2 | 1 | 2 | 5 | 14 |
| Ankle | Group 1 | An 9 | 1 | 1 | 1 | 0 | 0 | 3 |
| Ankle | Group 1 | An 10 | 3 | 1 | 1 | 1 | 4 | 16 |
| Ankle | Group 2 | An 1 | 0 | 1 | 0 | 0 | 0 | 1 |
| Ankle | Group 2 | An 2 | 0 | 0 | 0 | 0 | 0 | 0 |
| Ankle | Group 2 | An 3 | 0 | 0 | 0 | 0 | 0 | 0 |
| Ankle | Group 2 | An 4 | 0 | 0 | 0 | 0 | 0 | 0 |
| Ankle | Group 2 | An 5 | 0 | 0 | 0 | 0 | 0 | 0 |
| Ankle | Group 2 | An 6 | 1 | 0 | 0 | 0 | 0 | 1 |
| Ankle | Group 2 | An 7 | 0 | 0 | 0 | 0 | 0 | 0 |
| Ankle | Group 2 | An 8 | 0 | 0 | 0 | 0 | 0 | 0 |
| Ankle | Group 2 | An 9 | 0 | 0 | 0 | 0 | 0 | 0 |
| Ankle | Group 2 | An 10 | 0 | 0 | 0 | 0 | 0 | 0 |
| Ankle | Group 3 | An 1 | 3 | 2 | 1 | 1 | 4 | 11 |
| Ankle | Group 3 | An 2 | 0 | 0 | 0 | 0 | 0 | 0 |
| Ankle | Group 3 | An 3 | 0 | 0 | 0 | 0 | 0 | 0 |
| Ankle | Group 3 | An 4 | 3 | 4 | 2 | 3 | 4 | 16 |
| Ankle | Group 3 | An 5 | 3 | 4 | 2 | 3 | 3 | 15 |
| Ankle | Group 3 | An 6 | 0 | 0 | 0 | 0 | 0 | 0 |
| Ankle | Group 3 | An 7 | 0 | 0 | 0 | 0 | 0 | 0 |
| Ankle | Group 3 | An 8 | 1 | 0 | 0 | 0 | 0 | 1 |
| Ankle | Group 3 | An 9 | 3 | 2 | 1 | 0 | 0 | 4 |
| Ankle | Group 3 | An 10 | 2 | 2 | 1 | 3 | 3 | 11 |
| Ankle | Group 4 | An 1 | 0 | 1 | 0 | 0 | 0 | 1 |
| Ankle | Group 4 | An 2 | 1 | 1 | 1 | 1 | 0 | 4 |
| Ankle | Group 4 | An 3 | 2 | 2 | 1 | 0 | 0 | 5 |
| Ankle | Group 4 | An 4 | 2 | 0 | 1 | 0 | 0 | 2 |
| Ankle | Group 4 | An 5 | 0 | 0 | 0 | 0 | 0 | 0 |
| Ankle | Group 4 | An 6 | 3 | 3 | 2 | 2 | 3 | 13 |
| Ankle | Group 4 | An 7 | 0 | 1 | 0 | 0 | 0 | 1 |
| Ankle | Group 4 | An 8 | 1 | 1 | 1 | 0 | 0 | 3 |
| Ankle | Group 4 | An 9 | 1 | 0 | 0 | 0 | 0 | 1 |
| Ankle | Group 4 | An 10 | 0 | 0 | 0 | 0 | 0 | 0 |

Inflammation: 0 = normal; 1 = minimal infiltration of inflammatory cells in periarticular tissue; 2 = mild infiltration; 3 = moderate infiltration with moderate edema; 4 = marked infiltration with marked edema; 5 = severe infiltration with severe edema. Pannus: 0 = normal; 1 = minimal infiltration of pannus in cartilage and subchondral bone; 2 = mild infiltration; 3 = moderate infiltration; 4 = marked infiltration; 5 = severe infiltration. Cartilage damage: 0 = normal; 1 = minimal to mild loss of staining density with no obvious chondrocyte loss or collagen disruption; 2 = mild loss of staining density with focal mild (superficial) chondrocyte loss and/or collagen disruption; 3 = moderate loss of staining density with multifocal moderate (depth to middle zone) chondrocyte loss and/or collagen disruption; 4 = marked loss of staining density with multifocal marked (depth to deep zone) chondrocyte loss and/or collagen disruption; 5 = severe diffuse loss of staining density with multifocal severe (depth to tide mark) chondrocyte loss and/or collagen disruption. Bone resorption: 0 = normal; 1 = minimal; 2 = mild; 3 = moderate; 4 = marked; 5 = severe. Periosteal change/exostotic growth: 0 = normal; 1 = minimal; 2 = mild; 3 = moderate; 4 = marked; 5 = severe.

Figure 8:
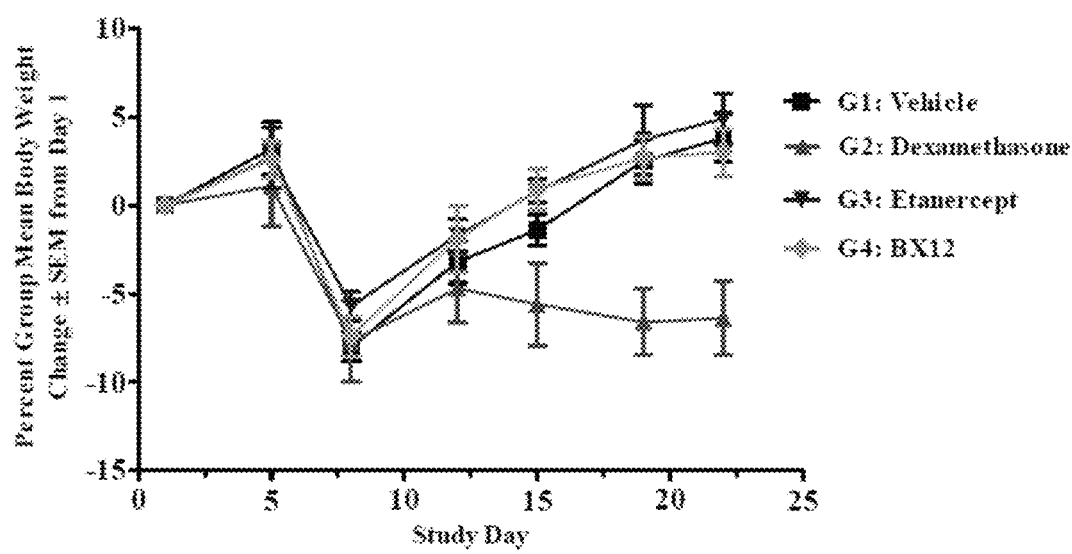
FIG. 8 illustrates percent group mean body weight change from day 1 in PK-e363. Bx-12=FH.

FH was well tolerated, as there were no treatment-related deaths, and body weights were comparable to vehicle controls (FIG. 8). Animals treated with FH displayed an improved clinical response compared to vehicle control animals (Tables 6 and 7).

TABLE 6

Total arthritic response at endpoint.

| Agent | Maximum Δ Mean Volume[1] | Mean Disease Burden[2] | % Disease Suppression (vs Vehicle)[2] | Mean Maximum Clinical Score[3] | Mean Body Weigh at Nadir[4] |
|---|---|---|---|---|---|
| Vehicle | 0.21 | 1.93 | — | 45.4 | −8.0% |
| Dexamethasone | 0.03*** | −0.32*** | 116.5 | 9.2*** | −7.7% |
| Etanercept | 0.13** | 0.74** | 61.7 | 39.6[ns] | −5.7% |
| Factor H | 0.12*** | 0.05*** | 97.3 | 33.4[ns] | −7.4% |

[1]Maximum Δ Mean Volume—difference (in ml) between the mean combined foot pad volumes recorded on day 8 and on median day of maximal swelling;
[2]Mean Disease Burden—determined by measuring an initial combined footpad volume for each animal (to establish a baseline), then integrating the AUC for the combined footpad volume over time (days 8 to 22) for each animal and then calculating the group mean; % Disease Suppression—percent decrease in total disease burden relative to vehicle;
[3]Mean Maximum Clinical Score—scored from 0 to 60 (15/limb), calculated as the sum of 4 limbs (5 points/paw for red or swollen digit, 5 points for each swollen foot pad and 5 points for each swollen ankle);
[4]Mean Body Weight Nadir—lowest group mean body weight as % change from day 1.
* = $P < 0.05$,
** = $P < 0.01$,
*** = $P < 0.001$.

TABLE 7

Clinical score
Clinical Score

| | | | | Date | | | | | |
|---|---|---|---|---|---|---|---|---|---|
| | Jun. 24, 2011 | Jun. 27, 2011 | Jun. 28, 2011 | Jun. 29, 2011 | Jul. 1, 2011 | Jul. 5, 2011 | Jul. 8, 2011 | | |
| | | | | Day of Study | | | | | Max |
| A# | 8 Score | 11 Score | 12 Score | 13 Score | 16 Score | 19 Score | 22 Score | Clin Score | Day |
| Group 1: vehicle (ip, qod x 7 (start on day 8)) | | | | | | | | | |
| 1 | 5 | 21 | 35 | 32 | 34 | 31 | 27 | 35 | 12 |
| 2 | 5 | 26 | 32 | 32 | 32 | 32 | 30 | 32 | 12 |
| 3 | 0 | 22 | 40 | 38 | 38 | 29 | 43 | 43 | 22 |
| 4 | 5 | 24 | 44 | 39 | 37 | 36 | 33 | 44 | 12 |
| 5 | 10 | 30 | 44 | 41 | 43 | 42 | 36 | 44 | 12 |
| 6 | 5 | 30 | 60 | 53 | 53 | 42 | 40 | 60 | 12 |
| 7 | 10 | 27 | 53 | 35 | 35 | 35 | 28 | 53 | 12 |
| 8 | 0 | 37 | 55 | 52 | 55 | 52 | 50 | 55 | 12 |
| 9 | 0 | 7 | 26 | 22 | 28 | 25 | 22 | 28 | 16 |
| 10 | 5 | 39 | 60 | 60 | 59 | 60 | 45 | 60 | 12 |
| Mean | 4.50 | 26.30 | 44.50 | 40.40 | 41.40 | 38.60 | 35.70 | 45.40 | 12.00 |
| SEM | 1.17 | 2.84 | 3.75 | 3.64 | 3.38 | 3.42 | 2.96 | 3.62 | 1.03 |
| n | 10 | 10 | 10 | 10 | 10 | 10 | 10 | 10 | 10 |
| Group 2: dexamethasone (3.32 mg/kg, po, qd x 14 (start on day 8)) | | | | | | | | | |
| 1 | 5 | 0 | 0 | 0 | 0 | 0 | 0 | 5 | 8 |
| 2 | 10 | 0 | 10 | 10 | 0 | 0 | 0 | 10 | 8 |
| 3 | 0 | 1 | 0 | 10 | 0 | 0 | 0 | 10 | 13 |
| 4 | 10 | 0 | 5 | 10 | 0 | 0 | 0 | 10 | 8 |
| 5 | 0 | 0 | 7 | 0 | 0 | 0 | 0 | 7 | 12 |
| 6 | 5 | 0 | 10 | 10 | 0 | 0 | 0 | 10 | 12 |
| 7 | 10 | 0 | 0 | 10 | 0 | 0 | 0 | 10 | 8 |
| 8 | 0 | 0 | 10 | 0 | 0 | 0 | 0 | 10 | 12 |
| 9 | 0 | 0 | 10 | 0 | 0 | 0 | 0 | 10 | 12 |
| 10 | 0 | 0 | 5 | 10 | 0 | 0 | 0 | 10 | 13 |
| Mean | 4.00 | 0.10 | 5.70 | 6.00 | 0.00 | 0.00 | 0.00 | 9.20 | 12.00 |
| SEM | 1.45 | 0.10 | 1.39 | 1.63 | 0.00 | 0.00 | 0.00 | 0.55 | 0.72 |
| n | 10 | 10 | 10 | 10 | 10 | 10 | 10 | 10 | 10 |
| Group 3: etanercept (10 mg/kg, ip, days 8, 10, 12, 15, 17, 19) | | | | | | | | | |
| 1 | 0 | 12 | 32 | 32 | 32 | 32 | 32 | 32 | 12 |
| 2 | 15 | 34 | 50 | 50 | 49 | 48 | 41 | 50 | 12 |
| 3 | 10 | 28 | 45 | 45 | 21 | 34 | 34 | 45 | 22 |
| 4 | 0 | 4 | 27 | 21 | 48 | 25 | 16 | 46 | 12 |
| 5 | 0 | 15 | 35 | 35 | 25 | 5 | 16 | 35 | 12 |

TABLE 7-continued

Clinical score
Clinical Score

| A# | Date Jun. 24, 2011 Day of Study 8 Score | Jun. 27, 2011 11 Score | Jun. 28, 2011 12 Score | Jun. 29, 2011 13 Score | Jul. 1, 2011 16 Score | Jul. 5, 2011 19 Score | Jul. 8, 2011 22 Score | Max Clin Score | Day |
|---|---|---|---|---|---|---|---|---|---|
| 6 | 10 | 43 | 50 | 45 | 45 | 45 | 40 | 50 | 12 |
| 7 | 0 | 11 | 26 | 30 | 15 | 20 | 19 | 30 | 12 |
| 8 | 0 | 10 | 20 | 15 | 10 | 10 | 10 | 20 | 12 |
| 9 | 10 | 12 | 34 | 34 | 24 | 26 | 23 | 34 | 16 |
| 10 | 10 | 27 | 52 | 48 | 46 | 37 | 26 | 52 | 12 |
| Mean | 5.50 | 19.60 | 37.10 | 35.50 | 31.50 | 28.40 | 25.70 | 39.60 | 12.00 |
| SEM | 1.89 | 3.98 | 3.61 | 3.69 | 4.61 | 4.41 | 3.39 | 3.43 | 1.03 |
| n | 10 | 10 | 10 | 10 | 10 | 10 | 10 | 10 | 10 |
| Group 4: BX12 (440 mg/kg, ip, qod x 7 (start on day 8)) | | | | | | | | | |
| 1 | 5 | 25 | 37 | 18 | 13 | 25 | 24 | 37 | 12 |
| 2 | 0 | 10 | 42 | 37 | 21 | 31 | 31 | 42 | 12 |
| 3 | 5 | 15 | 42 | 34 | 15 | 20 | 21 | 42 | 12 |
| 4 | 0 | 5 | 20 | 20 | 10 | 10 | 10 | 20 | 12 |
| 5 | 0 | 15 | 21 | 10 | 1 | 0 | 1 | 21 | 12 |
| 6 | 0 | 18 | 49 | 40 | 43 | 46 | 39 | 49 | 12 |
| 7 | 15 | 21 | 30 | 20 | 15 | 10 | 15 | 30 | 12 |
| 8 | 5 | 21 | 32 | 26 | 25 | 20 | 26 | 32 | 12 |
| 9 | 0 | 10 | 16 | 15 | 6 | 7 | 5 | 16 | 12 |
| 10 | 0 | 6 | 45 | 16 | 20 | 10 | 16 | 45 | 12 |
| Mean | 3.00 | 14.60 | 33.40 | 23.60 | 16.90 | 18.20 | 18.80 | 33.40 | 12.00 |
| SEM | 1.53 | 2.14 | 3.63 | 3.23 | 3.67 | 4.44 | 3.72 | 3.63 | 0.00 |
| n | 10 | 10 | 10 | 10 | 10 | 10 | 10 | 10 | 10 |

Figure 9:
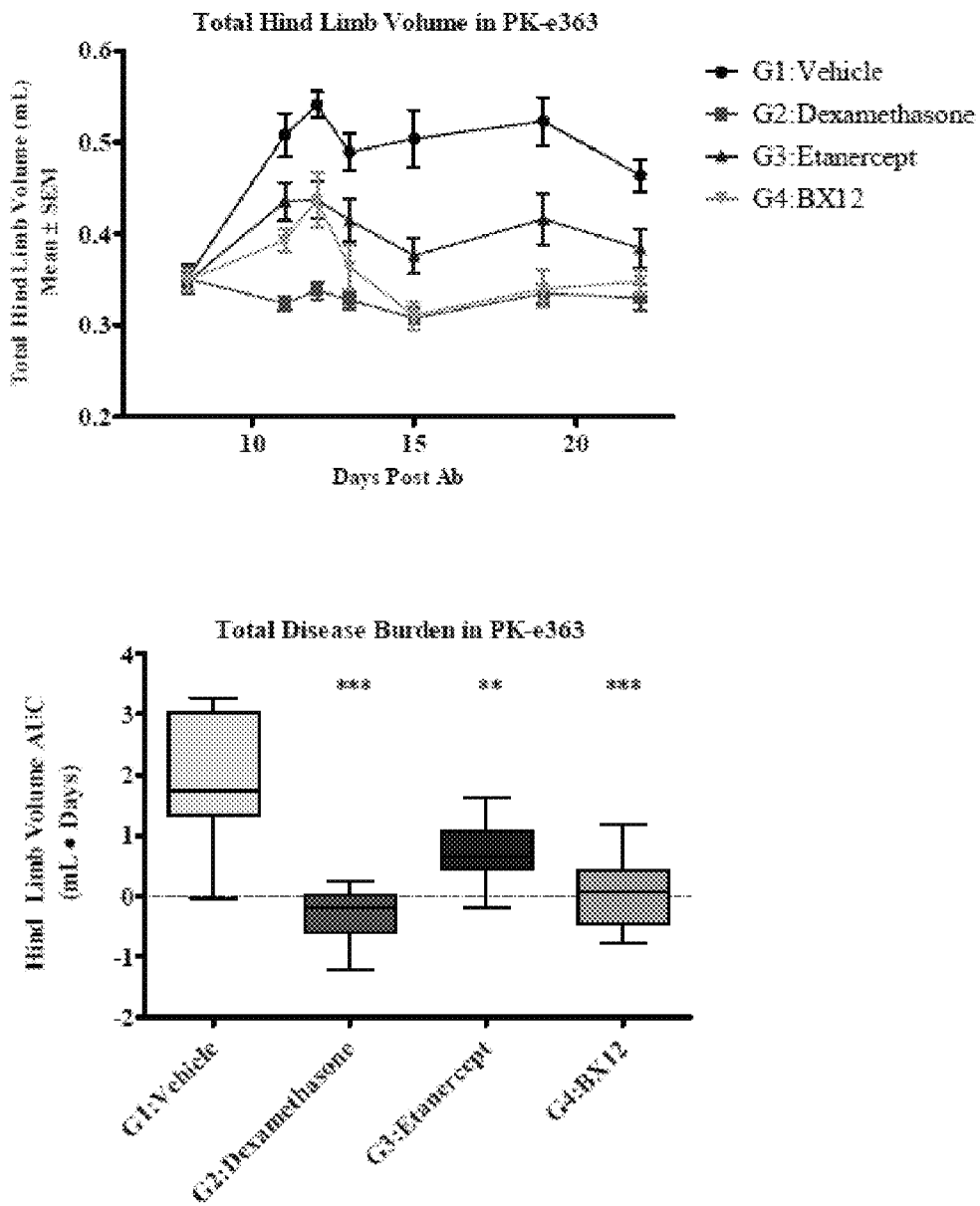
FIG. 9 illustrates the effect of test agents on total hind limb swelling in mouse CAIA in PK-e363. Bx-12=FH.
Figure 10:
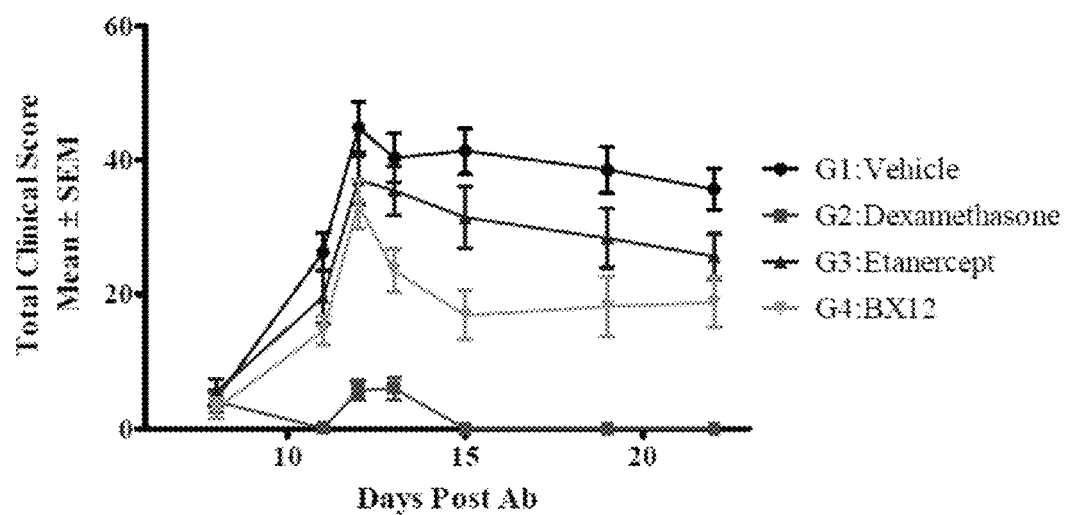
FIG. 10 illustrates the total clinical score for CAIA in PK-e363. Bx-12=FH.

The FH-treated mice displayed a lower mean change in foot pad swelling on the day of maximal swelling compared to vehicle (Table 9). In addition, FH performed well compared to Etanercept (FIG. 9; Bx-12=FH). FH improves more over Etanercept at later time points (days 15 to 22), suggesting that FH promotes rapid resolution of the inflammatory response in addition to inhibiting the initial inflammatory response (FIG. 10). The histopathology summary for the collagen antibody-induced arthritis is shown in Table 8 and statistical analysis shown in Table 10.

TABLE 8

Histopathology summary.

| Agent | Inflammation | Pannus | Cartilage Damage | Bone Resorption | Exostosis | Composite Score |
|---|---|---|---|---|---|---|
| Vehicle | 2.0 ± 0.5 | 1.0 ± 0.3 | 0.5 ± 0.2 | 0.6 ± 0.3 | 2.6 ± 0.5 | 6.7 ± 1.7 |
| Dex. | 0.1 ± 0.1** | 0.1 ± 0.1$^{ns}$ | 0 ± 0$^{ns}$ | 0 ± 0$^{ns}$ | 0 ± 0** | 0.2 ± 0.1* |
| Etanercept | 1.5 ± 0.5$^{ns}$ | 1.4 ± 0.5$^{ns}$ | 0.7 ± 0.3$^{ns}$ | 1.0 ± 0.4$^{ns}$ | 1.4 ± 0.6$^{ns}$ | 6.0 ± 2.1$^{ns}$ |
| Factor H | 1.0 ± 0.3$^{ns}$ | 0.9 ± 0.3$^{ns}$ | 0.6 ± 0.2$^{ns}$ | 0.3 ± 0.2$^{ns}$ | 0.3 ± 0.3* | 3.1 ± 1.2$^{ns}$ |

Inflammation - 1 = minimal infiltration of inflammatory cells (periarticularly), 2 = mild infiltration, 3- moderate infiltration + edema, 4 = marked infiltration&edema, 5 = severe infiltration&edema; Pannus- 1 = minimal infiltration of pannus in cartilage, 2 = mild infiltration, 3-moderate infiltration, 4 = marked infiltration, 5 = severe infiltration; Cartilage Resorption- graded 1-5 (minimal to severe) based on staining density, chondrocyte loss and collagen disruption; Bone Resorption- graded 1-5 based on areas of resorption, and osteoclast density; Exostosis- graded 1 to 5 based on appearance of a roughened perioteal surface and the presences of inflammatory cells, periostial cells or osteoblasts.
$^{ns}$ = not significant,
* = P < 0.05,
** = P < 0.01,
*** = P < 0.001.

Figure 11:
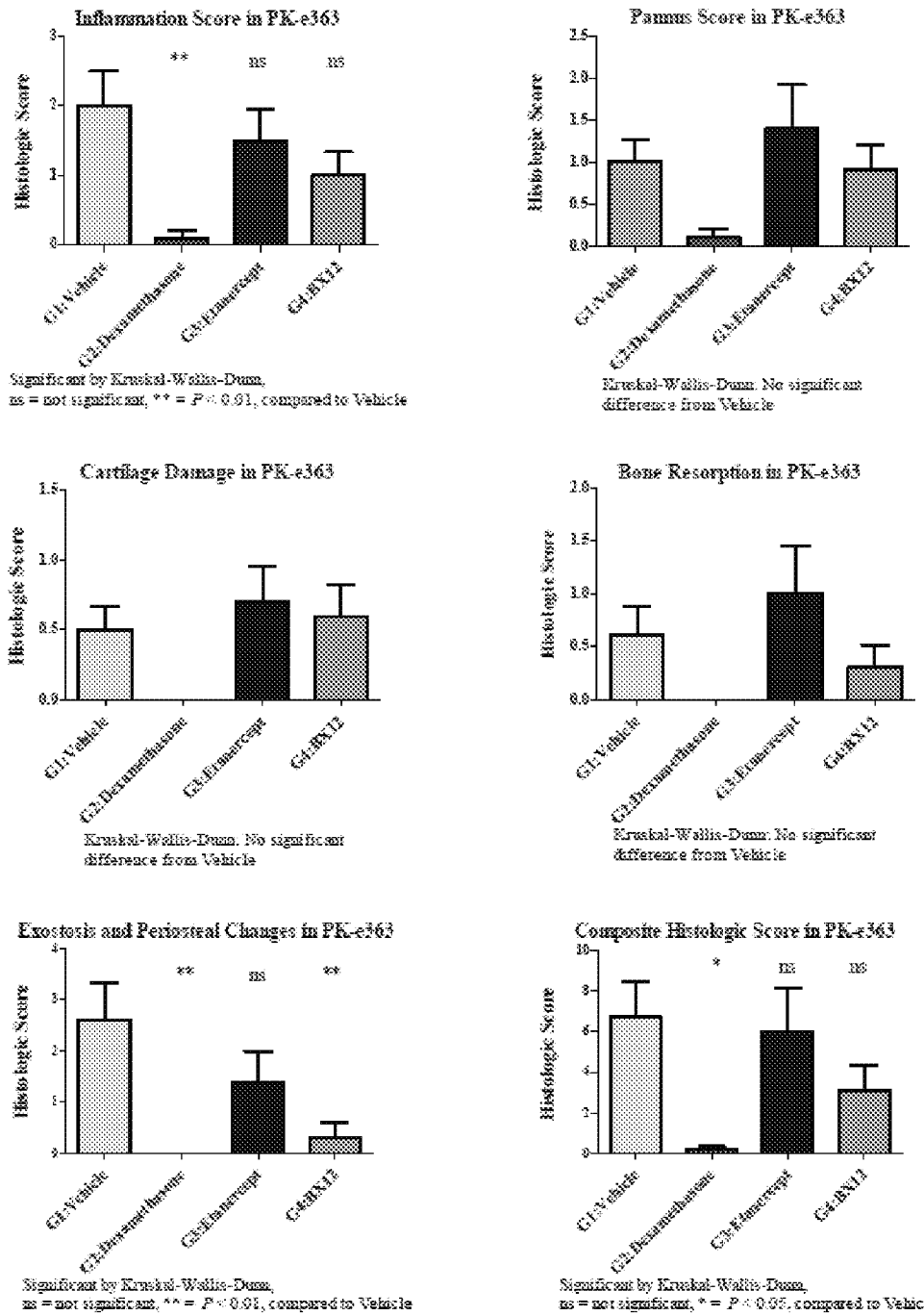
FIG. 11 illustrates the effect of test agents on histological changes in mouse CAIA in PK-e363. Bx-12=FH.

The Dexamethasone control consistently produced an improved histopathology result. FH inhibits exostosis (the inappropriate formation of new bone on the surface of bone) compared to both vehicle control and Etanercept. There was additionally a trend toward improved inflammation and bone resorption for FH-treated mice, resulting in a lower clinical score compared to both vehicle and Etanercept (FIG. 11). This RA animal model study suggests that Factor H is an effective therapeutic in limiting the complement-mediated inflammatory response in this disease setting.

TABLE 9

Footpad thickness.
Total Footpad Thickness

Group 1: vehicle (ip, qod x 7 (start on day 8))

| | | | | Date | | | | |
|---|---|---|---|---|---|---|---|---|
| | Jun. 24, 2011 | Jun. 27, 2011 | Jun. 28, 2011 | Jun. 29, 2011 | Jul. 1, 2011 | Jul. 5, 2011 | Jul. 8, 2011 | |
| | | | | Day of Study | | | | |
| A# | 8 mL | 11 mL | 12 mL | 13 mL | 116 mL | 19 mL | 22 mL | Total Disease Burden (AUC) |
| 1 | 0.44 | 0.57 | 0.53 | 0.53 | 0.58 | 0.55 | 0.49 | 1.37 |
| 2 | 0.39 | 0.41 | 0.48 | 0.38 | 0.36 | 0.34 | 0.43 | −0.03 |
| 3 | 0.39 | 0.57 | 0.59 | 0.51 | 0.54 | 0.53 | 0.48 | 1.82 |
| 4 | 0.36 | 0.48 | 0.53 | 0.43 | 0.42 | 0.55 | 0.55 | 1.85 |
| 5 | 0.36 | 0.48 | 0.51 | 0.41 | 0.52 | 0.52 | 0.44 | 1.59 |
| 6 | 0.33 | 0.65 | 0.8 | 0.56 | 0.55 | 0.8 | 0.54 | 3.18 |
| 7 | 0.33 | 0.44 | 0.58 | 0.55 | 0.58 | 0.51 | 0.39 | 2.27 |
| 8 | 0.31 | 0.56 | 0.57 | 0.53 | 0.55 | 0.58 | 0.47 | 3.00 |
| 9 | 0.31 | 0.45 | 0.47 | 0.45 | 0.31 | 0.43 | 0.39 | 1.21 |
| 10 | 0.3 | 0.48 | 0.55 | 0.54 | 0.61 | 0.82 | 0.46 | 3.26 |
| Mean | 0.35 | 0.51 | 0.54 | 0.49 | 0.50 | 0.52 | 0.46 | 1.93 |
| SEM | 0.01 | 0.02 | 0.01 | 0.02 | 0.03 | 0.03 | 0.02 | 0.32 |
| n | 10 | 10 | 10 | 10 | 10 | 10 | 10 | 10 |

| | | | | Date | | | | | |
|---|---|---|---|---|---|---|---|---|---|
| | Jun. 24, 2011 | Jun. 27, 2011 | Jun. 28, 2011 | Jun. 29, 2011 | Jul. 1, 2011 | Jul. 5, 2011 | Jul. 8, 2011 | Total Disease | % Disease |
| | | | | Day of Study | | | | Burden | Suppres- |
| A# | 8 mL | 11 mL | 12 mL | 13 mL | 16 mL | 19 mL | 22 mL | (AUC) | sion |

Group 2: dexamethasone (3.32 mg/kg, po, qd x 14 (start on day 8))

| A# | 8 mL | 11 mL | 12 mL | 13 mL | 16 mL | 19 mL | 22 mL | AUC | % |
|---|---|---|---|---|---|---|---|---|---|
| 1 | 0.42 | 0.38 | 0.34 | 0.31 | 0.37 | 0.35 | 0.39 | −0.77 | 139.7 |
| 2 | 0.39 | 0.34 | 0.34 | 0.3 | 0.33 | 0.35 | 0.42 | −0.56 | 129.0 |
| 3 | 0.39 | 0.32 | 0.28 | 0.3 | 0.29 | 0.28 | 0.3 | −1.21 | 162.5 |
| 4 | 0.37 | 0.3 | 0.35 | 0.31 | 0.38 | 0.3 | 0.32 | −0.54 | 125.0 |
| 5 | 0.35 | 0.3 | 0.32 | 0.36 | 0.29 | 0.38 | 0.29 | −0.28 | 114.5 |
| 6 | 0.34 | 0.32 | 0.34 | 0.35 | 0.29 | 0.37 | 0.35 | −0.05 | 102.9 |
| 7 | 0.33 | 0.35 | 0.31 | 0.33 | 0.26 | 0.35 | 0.35 | −0.09 | 104.7 |
| 8 | 0.31 | 0.31 | 0.34 | 0.38 | 0.3 | 0.35 | 0.31 | 0.25 | 87.3 |
| 9 | 0.31 | 0.3 | 0.39 | 0.35 | 0.3 | 0.32 | 0.29 | 0.10 | 95.1 |
| 10 | 0.3 | 0.32 | 0.37 | 0.29 | 0.27 | 0.3 | 0.26 | −0.02 | 101.3 |
| Mean | 0.35 | 0.32 | 0.34 | 0.33 | 0.31 | 0.34 | 0.33 | −0.32 | 116.49 |
| SEM | 0.01 | 0.01 | 0.01 | 0.01 | 0.01 | 0.01 | 0.01 | 0.14 | 7.51 |
| n | 10 | 10 | 10 | 10 | 10 | 10 | 10 | 10 | 10 |

Group 3: etanercept (10 mg/kg, ip, days 8, 10, 12, 15, 17, 19)

| A# | 8 mL | 11 mL | 12 mL | 13 mL | 16 mL | 19 mL | 22 mL | AUC | % |
|---|---|---|---|---|---|---|---|---|---|
| 1 | 0.41 | 0.49 | 0.58 | 0.58 | 0.45 | 0.61 | 0.55 | 1.62 | 16.3 |
| 2 | 0.4 | 0.44 | 0.44 | 0.41 | 0.46 | 0.43 | 0.41 | 0.58 | 74.3 |
| 3 | 0.38 | 0.37 | 0.35 | 0.36 | 0.34 | 0.4 | 0.34 | −0.19 | 109.8 |
| 4 | 0.37 | 0.38 | 0.42 | 0.33 | 0.37 | 0.47 | 0.39 | 0.35 | 81.9 |
| 5 | 0.35 | 0.59 | 0.46 | 0.49 | 0.43 | 0.32 | 0.34 | 0.92 | 52.3 |
| 6 | 0.34 | 0.4 | 0.49 | 0.41 | 0.41 | 0.42 | 0.41 | 0.97 | 49.7 |
| 7 | 0.32 | 0.4 | 0.45 | 0.39 | 0.33 | 0.35 | 0.36 | 0.59 | 69.4 |
| 8 | 0.31 | 0.44 | 0.39 | 0.35 | 0.32 | 0.33 | 0.36 | 0.58 | 70.2 |
| 9 | 0.3 | 0.45 | 0.4 | 0.43 | 0.33 | 0.47 | 0.36 | 1.37 | 29.0 |
| 10 | 0.3 | 0.41 | 0.39 | 0.4 | 0.3 | 0.36 | 0.32 | 0.70 | 63.7 |
| Mean | 0.35 | 0.44 | 0.44 | 0.42 | 0.38 | 0.42 | 0.38 | 0.74 | 61.66 |
| SEM | 0.01 | 0.02 | 0.02 | 0.02 | 0.02 | 0.03 | 0.02 | 0.16 | 8.42 |
| n | 10 | 10 | 10 | 10 | 10 | 10 | 10 | 10 | 10 |

Group 4: BX12 (440 mg/kg, ip, qod x 7 (start on day 8))

| A# | 8 mL | 11 mL | 12 mL | 13 mL | 16 mL | 19 mL | 22 mL | AUC | % |
|---|---|---|---|---|---|---|---|---|---|
| 1 | 0.41 | 0.44 | 0.5 | 0.32 | 0.29 | 0.3 | 0.38 | −0.78 | 140.2 |
| 2 | 0.4 | 0.36 | 0.56 | 0.54 | 0.35 | 0.4 | 0.39 | 0.13 | 93.5 |
| 3 | 0.38 | 0.38 | 0.52 | 0.36 | 0.29 | 0.42 | 0.32 | −0.15 | 107.8 |
| 4 | 0.37 | 0.4 | 0.4 | 0.32 | 0.32 | 0.31 | 0.32 | −0.42 | 121.6 |
| 5 | 0.35 | 0.34 | 0.35 | 0.29 | 0.28 | 0.25 | 0.33 | −0.60 | 130.8 |
| 6 | 0.34 | 0.39 | 0.55 | 0.43 | 0.42 | 0.45 | 0.42 | 1.19 | 38.3 |
| 7 | 0.32 | 0.46 | 0.37 | 0.29 | 0.27 | 0.29 | 0.35 | 0.08 | 96.1 |
| 8 | 0.32 | 0.43 | 0.34 | 0.37 | 0.28 | 0.29 | 0.34 | 0.08 | 96.9 |
| 9 | 0.3 | 6.39 | 0.3 | 0.39 | 0.35 | 0.36 | 0.29 | 0.55 | 65.5 |
| 10 | 0.3 | 0.35 | 0.45 | 0.33 | 0.28 | 0.3 | 0.34 | 0.35 | 52.1 |

TABLE 9-continued

Footpad thickness.
Total Footpad Thickness

| Mean | 0.35 | 0.39 | 0.44 | 0.36 | 0.31 | 0.34 | 0.35 | 0.05 | 97.33 |
|---|---|---|---|---|---|---|---|---|---|
| SEM | 0.01 | 0.01 | 0.03 | 0.02 | 0.02 | 0.02 | 0.01 | 0.19 | 9.56 |
| n | 10 | 10 | 10 | 10 | 10 | 10 | 10 | 10 | 10 |

TABLE 10

Statistical analysis.

| One-way analysis of variance | Hind Limb Volume | | |
|---|---|---|---|
| P value | <0.0001 | | |
| P value summary | **** | | |
| Are means signif. different? ($P < 0.05$) | Yes | | |
| Number of groups | 4 | | |
| F | 17.58 | | |
| R square | 0.6872 | | |
| Bartlett's test for equal variances | | | |
| Bartlett's statistic (corrected) | 10.84 | | |
| P value | 0.0126 | | |
| P value summary | * | | |
| Do the variances differ signif. ($P < 0.05$) | Yes | | |
| ANOVA Table | SS | df | MS |
| Treatment (between columns) | 0.09067 | 3 | 0.03022 |
| Residual (within columns) | 0.04126 | 24 | 0.001719 |
| Total | 0.1319 | 27 | |

| Dunnett's Multiple Comparison Test | Mean Diff. | q | Significant? $P < 0.05$? | Summary | 95% CI of diff |
|---|---|---|---|---|---|
| Vehicle vs Dexamethasone | 0.1524 | 6.877 | Yes | *** | 0.09687 to 0.2080 |
| Vehicle vs Etanercept | 0.08143 | 3.674 | Yes | ** | 0.02587 to 0.1370 |
| Vehicle vs BX12 | 0.1199 | 5.408 | Yes | *** | 0.06430 to 0.1754 |

| One-way analysis of variance | Total Disease | | |
|---|---|---|---|
| P value | <0.0001 | | |
| P value summary | **** | | |
| Are means signif. different? ($P < 0.05$) | Yes | | |
| Number of groups | 4 | | |
| F | 21 | | |
| R square | 0.636 | | |
| Bartlett's test for equal variances | | | |
| Bartlett's statistic (corrected) | 7.61 | | |
| P value | 0.0548 | | |
| P value summary | ns | | |
| Do the variances differ signif. ($P < 0.05$) | No | | |
| ANOVA Table | SS | df | MS |
| Treatment (between columns) | 29.4 | 3 | 9.78 |
| Residual (within columns) | 16.8 | 36 | 0.467 |
| Total | 46.2 | 39 | |

| Dunnett's Multiple Comparison Test | Mean Diff. | q | Significant? $P < 0.05$? | Summary | 95% CI of diff |
|---|---|---|---|---|---|
| G1: Vehicle vs G2: Dexamethasone | 2.25 | 7.36 | Yes | *** | 1.50 to 3.00 |
| G1: Vehicle vs G3: Etanercept | 1.19 | 3.9 | Yes | ** | 0.441 to 1.94 |
| G1: Vehicle vs G4: BX12 | 1.88 | 6.15 | Yes | *** | 1.13 to 2.63 |

| Kruskal-Wallis test | Clinical Score |
|---|---|
| P value | <0.0001 |
| Exact or approximate P value? | Gaussian Approximation |
| P value summary | **** |
| Do the medians vary signif. ($P < 0.05$) | Yes |
| Number of groups | 4 |
| Kruskal-Wallis statistic | 24.71 |

TABLE 10-continued

Statistical analysis.

| Dunn's Multiple Comparison Test | Difference in rank sum | Significant? P < 0.05? | Summary |
|---|---|---|---|
| G1: Vehicle vs G2: Dexamethasone | 23.95 | Yes | *** |
| G1: Vehicle vs G3: Etanercept | 3.55 | No | ns |
| G1: Vehicle vs G4: BX12 | 8.3 | No | ns |

| Kruskal-Wallis test | Inflammation | Pannus | Cartilage |
|---|---|---|---|
| P value | 0.0154 | 0.0544 | 0.054 |
| Exact or approximate P value? | Gaussian Approximatio | Gaussian Approximatio | Gaussian Approximatio |
| P value summary | * | ns | ns |
| Do the medians vary signif. (P < 0.05) | Yes | No | No |
| Number of groups | 4 | 4 | 4 |
| Kruskal-Wallis statistic | 10.41 | 7.625 | 7.642 |

| Dunn's Multiple Comparison Test | Difference in rank sum | Significant? P < 0.05? | Summary | Difference in rank sum | Significant? P < 0.05? | Summary | Difference in rank sum | Significant? P < 0.05? | Summary |
|---|---|---|---|---|---|---|---|---|---|
| G1: Vehicle vs G2: Dexamethasone | 14.95 | Yes | ** | 11.4 | No | ns | 9.25 | No | ns |
| G1: Vehicle vs G3: Etanercept | 3.6 | No | ns | 0.3 | No | ns | −1.5 | No | ns |
| G1: Vehicle vs G4: BX12 | 6.45 | No | ns | 1.9 | No | ns | −0.75 | No | ns |

| Kruskal-Wallis test | Bone Resorption | Exostosis | Composite |
|---|---|---|---|
| P value | 0.1142 | 0.0054 | 0.0242 |
| Exact or approximate P value? | Gaussian Approximatio | Gaussian Approximatio | Gaussian Approximatio |
| P value summary | ns | ** | * |
| Do the medians vary signif. (P < 0.05) | No | Yes | Yes |
| Number of groups | 4 | 4 | 4 |
| Kruskal-Wallis statistic | 5.948 | 12.66 | 9.415 |

| Dunn's Multiple Comparison Test | Difference in rank sum | Significant? P < 0.05? | Summary | Difference in rank sum | Significant? P < 0.05? | Summary | Difference in rank sum | Significant? P < 0.05? | Summary |
|---|---|---|---|---|---|---|---|---|---|
| G1: Vehicle vs G2: Dexamethasone | No post-hoc tests | | | 13.1 | Yes | ** | 14.05 | Yes | * |
| G1: Vehicle vs G3: Etanercept | | | | 5.8 | No | ns | 2.1 | No | ns |
| G1: Vehicle vs G4: BX12 | | | | 11.5 | Yes | * | 3.25 | No | ns |

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual* and *Molecular Cloning: A Laboratory Manual* (all from Cold Spring Harbor Laboratory Press), Stryer, L. (1995) *Biochemistry* (4th Ed.) Freeman, Highly stabilized York, Gait, "*Oligonucleotide Synthesis: A Practical Approach*" 1984, IRL Press, London, Nelson and Cox (2000), Lehninger, *Principles of Biochemistry* $3^{rd}$ Ed., W. H. Freeman Pub., Highly stabilized York, N.Y. and Berg et al. (2002) *Biochemistry*, $5^{th}$ Ed., W. H. Freeman Pub., Highly stabilized York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the above description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Although the present invention is described primarily with reference to specific embodiments, it is also envisioned that other embodiments will become apparent to those skilled in the art upon reading the present disclosure, and it is intended that such embodiments be contained within the present inventive methods.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features which may be readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

What is claimed is:

1. A method for treating rheumatoid arthritis in a subject in need thereof, said method comprising administering a composition comprising Factor H (FH) to said subject, wherein said FH comprises SEQ ID NO: 1.

2. The method of claim 1, wherein said FH is a recombinant FH.

3. The method of claim 1, wherein said FH is a protective variant.

4. The method of claim 1, wherein said FH is administered to said subject intravenously.

5. The method of claim 1, wherein said FH is administered to said subject by intra-articular injection.

6. The method of claim 5, wherein said injection is to a joint of a member selected from the group consisting of: hand, foot, cervical spine, shoulder and knee.

7. The method of claim 1, wherein the method comprises reducing joint inflammation in said subject.

8. The method of claim 1, wherein the method comprises inhibiting an initial inflammatory response in said subject.

9. The method of claim 1, wherein the method comprises promoting resolution of an inflammatory response in said subject.

10. The method of claim 1, wherein the method comprises reducing exostosis in said subject.

11. The method of claim 1, wherein the method comprises reducing damage to cartilage in said subject as compared to a subject that has not received FH.

12. The method of claim 1, wherein said composition further comprises a plasma-derived FH.

13. The method of claim 1, wherein said FH is administered in an amount effective to reduce damage to cartilage in the subject as compared to a subject that has not received said FH.

14. The method of claim 1, wherein said FH is administered in a therapeutically effective dose between 0.05 mg/mL and 10 mg/mL.

15. The method of claim 1, wherein said FH is administered in a therapeutically effective dose between 0.1 mg/mL and 10 mg/mL.

16. The method of claim 1, wherein said FH composition for administration comprises an FH protein concentration of between 10 g/L and 250 g/L.

17. The method of claim 1, wherein said FH is administered in a therapeutically effective dose that results in a plasma level concentration in the subject of 0.05 mg/mL and 10 mg/mL.

18. The method of claim 1, wherein said FH is administered in a therapeutically effective dose that results in a plasma level concentration in the subject of between 0.1 mg/mL and 10 mg/mL.

19. The method of claim 1, wherein said FH is administered in a therapeutically effective dose that results in a plasma level concentration in the subject of between 0.1 mg/mL and 5 mg/mL.

20. The method of claim 1, wherein said FH is administered in a therapeutically effective dose that results in a plasma level concentration in the subject of between 1 mg/mL and 2 mg/mL.

21. The method of claim 1, wherein said FH is administered to the subject in a therapeutically effective dose of 50 mg/kg to 150 mg/kg.

* * * * *